United States Patent
Ota et al.

(10) Patent No.: US 9,457,118 B2
(45) Date of Patent: Oct. 4, 2016

(54) CORONA DISCHARGE DEVICE AND AIR-CONDITIONING APPARATUS

(71) Applicant: Mitsubishi Electric Corporation, Chiyoda-ku (JP)

(72) Inventors: Koji Ota, Chiyoda-ku (JP); Yasutaka Inanaga, Chiyoda-ku (JP); Akira Morikawa, Chiyoda-ku (JP); Takahiro Sakai, Chiyoda-ku (JP); Yasuhiro Tanimura, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 148 days.

(21) Appl. No.: 14/396,556

(22) PCT Filed: Apr. 3, 2013

(86) PCT No.: PCT/JP2013/060244
§ 371 (c)(1),
(2) Date: Oct. 23, 2014

(87) PCT Pub. No.: WO2013/161534
PCT Pub. Date: Oct. 31, 2013

(65) Prior Publication Data
US 2015/0290352 A1    Oct. 15, 2015

(30) Foreign Application Priority Data
Apr. 23, 2012    (JP) .................. 2012-097785

(51) Int. Cl.
*A62B 7/08*    (2006.01)
*A61L 9/16*    (2006.01)
(Continued)

(52) U.S. Cl.
CPC .. *A61L 9/16* (2013.01); *A61L 2/00* (2013.01); *A61L 9/00* (2013.01); *B03C 3/09* (2013.01);
(Continued)

(58) Field of Classification Search
CPC .. A61L 9/16; F24F 3/1603; F24F 2003/1635
USPC ....................................... 422/121
See application file for complete search history.

(56) References Cited

FOREIGN PATENT DOCUMENTS

| CN | 1907573 A | 2/2007 |
|---|---|---|
| CN | 200967020 Y | 10/2007 |
| JP | 58-26020 | 6/1983 |
| JP | 04-018944 | 1/1992 |
| JP | 04-171064 | 6/1992 |
| JP | 08-010650 | 1/1996 |
| JP | 08-112551 | 5/1996 |
| JP | 3066106 | 2/2000 |
| JP | 2005-152863 | 6/2005 |
| JP | 2005-205405 | 8/2005 |
| JP | 2010-022999 | 2/2010 |

OTHER PUBLICATIONS

Combined Chinese Office Action and Search Report issued Dec. 23, 2015 in Patent Application No. 201380026558.0 (with English language translation and English translation of categories documents).

(Continued)

*Primary Examiner* — Kevin Joyner
(74) *Attorney, Agent, or Firm* — Oblon, McClelland, Maier & Neustadt, L.L.P.

(57) ABSTRACT

A corona discharge device includes a charging-section high-voltage electrode unit including a plurality of charging-section high-voltage electrodes, and a charging-section ground electrode unit includes a plurality of charging-section ground electrodes formed by flat plates. The plurality of charging-section high-voltage electrodes are arranged at intervals in a direction intersecting an airflow in an air path, and are connected to one another at at least one longitudinal end by a conductive frame portion. The plurality of charging-section ground electrodes are disposed between the charging-section high-voltage electrodes in an orientation such that flat surfaces thereof are substantially parallel to the airflow in the air path, and are connected at at least one longitudinal end by a conductive frame portion. The plurality of charging-section high-voltage electrodes and the plurality of charging-section ground electrodes are alternately stacked in the direction intersecting the airflow in the air path to be spaced apart from each other.

7 Claims, 25 Drawing Sheets

(51) Int. Cl.
*B03C 3/41* (2006.01)
*B03C 3/09* (2006.01)
*B03C 3/12* (2006.01)
*B03C 3/36* (2006.01)
*B03C 3/47* (2006.01)
*F24F 3/16* (2006.01)
*A61L 2/00* (2006.01)
*A61L 9/00* (2006.01)

(52) U.S. Cl.
CPC ............... *B03C 3/12* (2013.01); *B03C 3/368* (2013.01); *B03C 3/41* (2013.01); *B03C 3/47* (2013.01); *F24F 3/1603* (2013.01); *F24F 3/166* (2013.01); *F24F 2003/1635* (2013.01); *F24F 2003/1682* (2013.01)

(56) References Cited

OTHER PUBLICATIONS

International Search Report issued Jul. 9, 2013 in PCT/JP13/060244 Filed Apr. 3, 2013.
Office Action issued May 24, 2016 in Chinese Patent Application No. 201380026558.0 (with English language translation).

FIG. 4
(a)
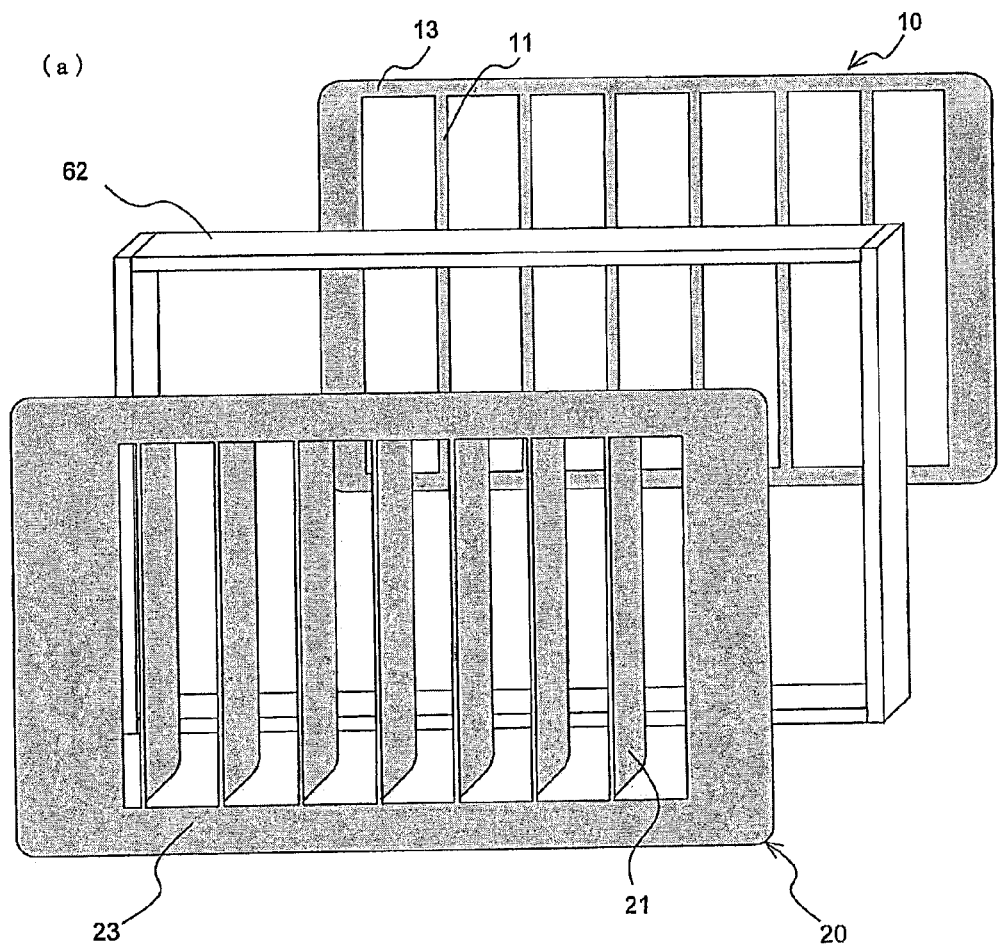
(b)
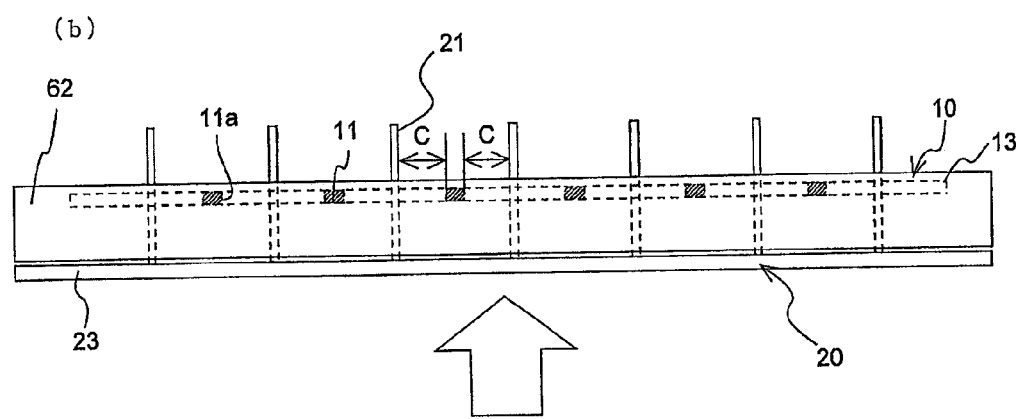

FIG. 5
(a)
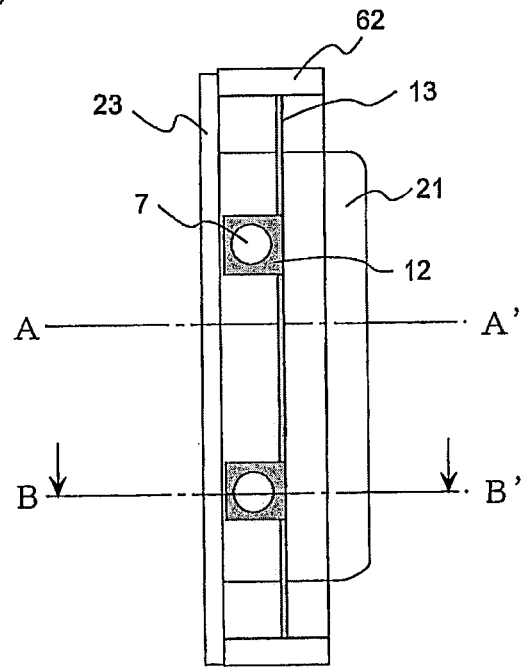
(b)
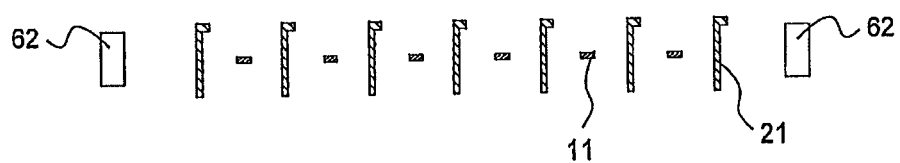
(c)
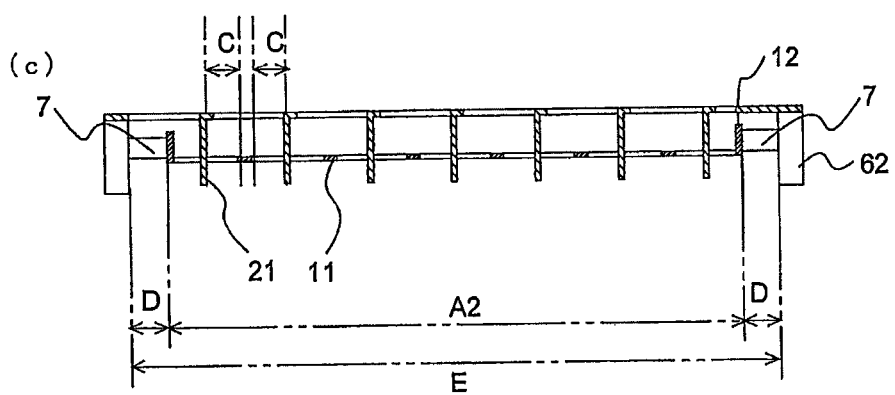

F I G. 1 5
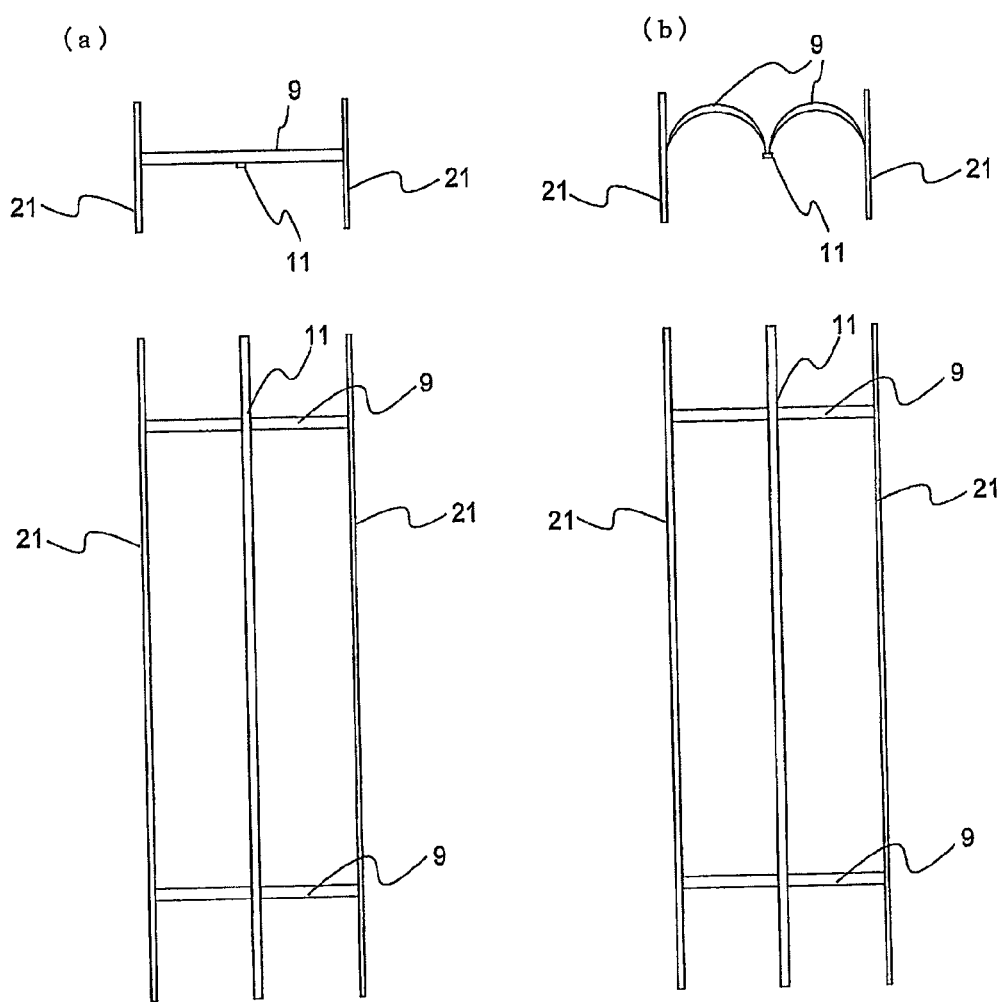

F I G. 2 1
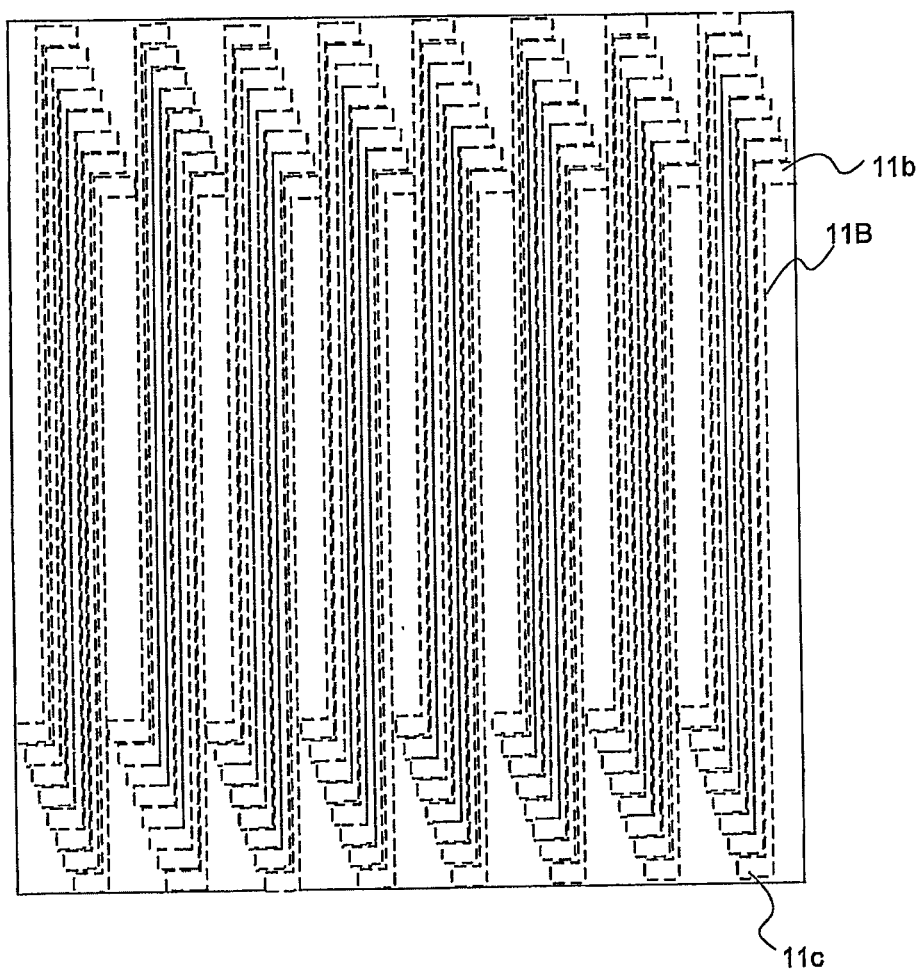

FIG. 24
(a)
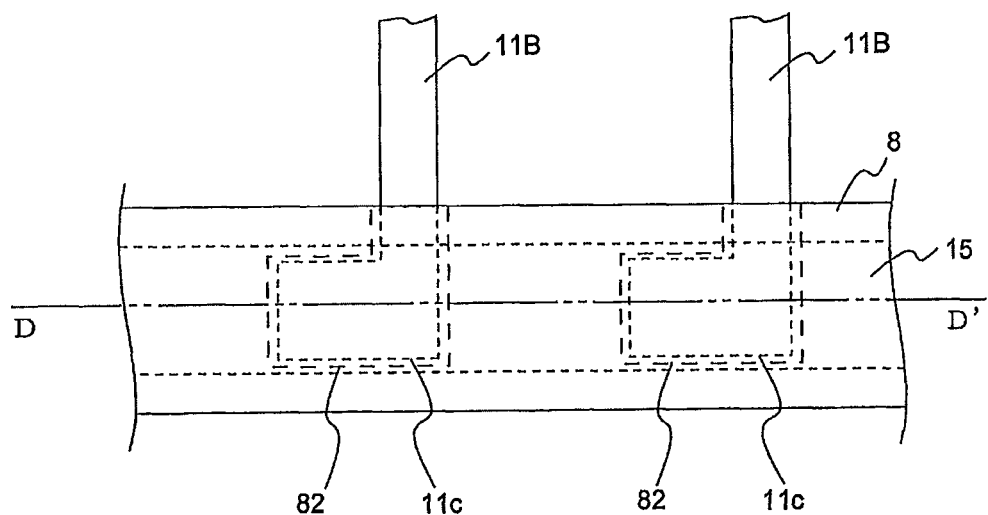
(b)
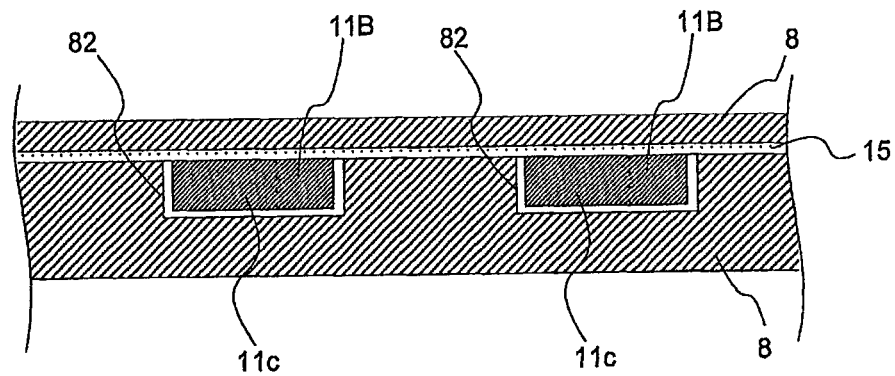

CORONA DISCHARGE DEVICE AND AIR-CONDITIONING APPARATUS

TECHNICAL FIELD

The present invention relates to a corona discharge device for use in an electric dust collection device, a deodorization device, a sterilization device, a virus removing device, and so on, and to an air-conditioning apparatus including this corona discharge device.

BACKGROUND ART

Conventionally, electric dust collection devices and deodorization devices adopt a technique of providing a corona discharge unit for bringing dust into a charged state by corona discharge and capturing the charged dust by a dust collector. In general, this corona discharge unit is configured to apply high voltage to discharge electrodes formed by wire electrodes having a wire diameter of about 0.1 mm to 1.0 mm so as to generate corona discharge between the discharge electrodes and counter electrodes. The thinner the used wire electrodes are, the lower the applied voltage for generating discharge can be. However, when the thin wires are used, local discharge and disconnection may be caused by, for example, corrosion or sputtering. To effectively collect dust, charge needs to be applied to almost all amount of air containing the dust. For this reason, it is preferable to increase the surface area of the discharge electrodes.

In the context of such matters, there has been proposed a discharge electrode that is formed by radially etching or press-cutting a quadrangular thin stainless steel plate having a thickness of 0.1 mm to 0.2 mm (see, for example, Patent Literature 1).

There have also been proposed plate-shaped (ribbon-shaped) discharge electrodes that are made of metal, such as tungsten, and that are disposed between counter electrodes with spaces therebetween (see, for example, Patent Literature 2).

CITATION LIST

Patent Literature

Patent Literature 1: Japanese Examined Utility Model Registration Application Publication No. 58-26020 (for example, page 1, lines 17 to 30, FIG. 2)

Patent Literature 2: Japanese Unexamined Patent Application Publication No. 2010-22999 (for example, page 3, FIG. 1)

SUMMARY OF INVENTION

Technical Problem

However, in the corona discharge electrode described in Patent Literature 1, a direction of an electric field for generating discharge is parallel to an air flowing direction. Hence, part of the air does not touch electrons and ions generated by discharge. Further, since discharge is not generated in a power feed unit for feeding power to the discharge electrode, air passing through such a non-discharge portion cannot be charged. This lowers charging efficiency.

In the charging device described in Patent Literature 2, since the discharge electrodes are plate-shaped (ribbon-shaped), the strength thereof is higher than that of thin wire electrodes. However, to dispose, in an air path, the plural discharge electrodes and the plural counter electrodes described in Patent Literature 2, there is a need to stretch the discharge electrodes and the counter electrodes one by one across a frame. Hence, production is troublesome.

The present invention has been made to solve the above-described problems, and provides a corona discharge device that is capable of stable corona discharge and is easy to assemble.

Solution to Problem

A corona discharge device according to the present invention includes an air-path housing having an air path therein, a discharge electrode unit including a plurality of first discharge electrodes each of which is formed by either of thin wire and flat plate having conductivity, and a counter electrode unit formed by a conductive flat plate. The counter electrode unit includes a plurality of counter electrodes formed by flat plates. The plurality of first discharge electrodes are arranged at intervals in a direction intersecting an airflow in the air path, and are connected to one another at at least one longitudinal end by a conductive frame. The plurality of counter electrodes of the counter electrode unit are disposed between the first discharge electrodes in an orientation such that flat surfaces thereof are substantially parallel to the airflow in the air path. The plurality of counter electrodes are connected to one another at at least one longitudinal end by a conductive frame. The counter electrodes and the first discharge electrodes are alternately stacked in the direction intersecting the airflow in the air path so as to be spaced apart from each other.

Advantageous Effects of Invention

The corona discharge device according to the present invention has high charging efficiency, and facilitates assembly of the first discharge electrodes and the counter electrodes.

BRIEF DESCRIPTION OF DRAWINGS

FIG. 4 includes explanatory views illustrating a structure of a charging section according to Embodiment 1.

FIG. 5 includes explanatory views illustrating an assembly manner of the charging-section high-voltage electrodes and the charging-section ground electrodes in Embodiment 1.

FIG. 15 illustrates charging-section high-voltage electrodes and charging-section ground electrodes according to Embodiment 4.

FIG. 21 illustrates an exemplary arrangement in a case in which charging-section high-voltage electrodes of Embodiment 7 are cut out of a single plate.

FIG. 24 illustrates a structure of portions where the charging-section high-voltage electrodes of Embodiment 7 are assembled to the insulating body.

DESCRIPTION OF EMBODIMENTS

Figure 1:
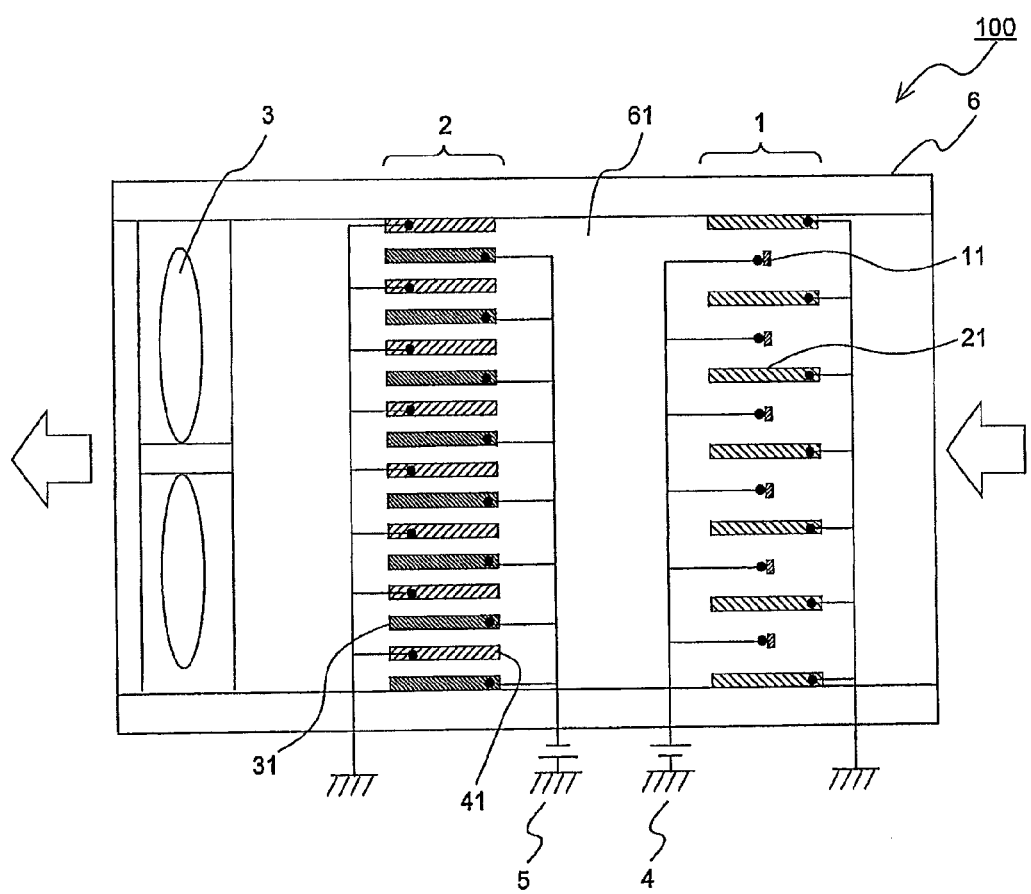
FIG. 1 is a schematic view of a corona discharge device according to Embodiment 1.

Embodiments of a corona discharge device according to the present invention will be described below with reference to the drawings. In the following description, terms representing directions (for example, ("up", "down", "right", "left", "front", and "rear") are appropriately used for easy understanding. However, these terms are used for description, but do not limit the present invention. In Embodiments, the same or substantially identical structures are denoted by the same reference numerals.

Embodiment 1

FIG. 1 is a schematic view of a corona discharge device (hereinafter referred to as a device 100) according to Embodiment 1. With reference to FIG. 1, the structure and operation of the device 100 will be described. In FIG. 1 and subsequent drawings, the dimensional relationships among components are sometimes different from the actual ones. Further, in FIG. 1, the flow of air is shown by arrows.

[Device 100]

The device 100 is an electric dust collection device that cleans the space by capturing particles (hereinafter referred to as suspended particles) and microbes and viruses (hereinafter suspended microbes) that are suspended in air flowing in the device 100 and supplying the air to the outside after the suspended particles and suspended microbes are captured from the air. The device 100 includes an air-path housing 6 having therein an air path 61 through which air flows. In the air path 61, a charging section 1, a capturing section 2, and a fan 3 are disposed.

The charging section 1 includes a plurality of charging-section high-voltage electrodes 11 serving as first discharge electrodes, and a plurality of charging-section ground electrodes 21 serving as counter electrodes of the charging-section high-voltage electrodes 11. To the charging-section high-voltage electrodes 11, voltage is applied from a charging high-voltage power supply 4.

The capturing section 2 includes a plurality of capturing-section high-voltage electrodes 31 serving as second discharge electrodes, and a plurality of capturing-section ground electrodes 41 serving as counter electrodes of the capturing-section high-voltage electrodes 31. To the capturing-section high-voltage electrodes 31, voltage is applied from a capturing high-voltage power supply 5.

The fan 3 introduces air into the air-path housing 6, and sends out the introduced air. In an airflow formed by the fan 3, the charging section 1 is disposed on an upstream side and the capturing section 2 is disposed downstream of the charging section 1.

[Charging-Section High-Voltage Electrode]

Figure 2:
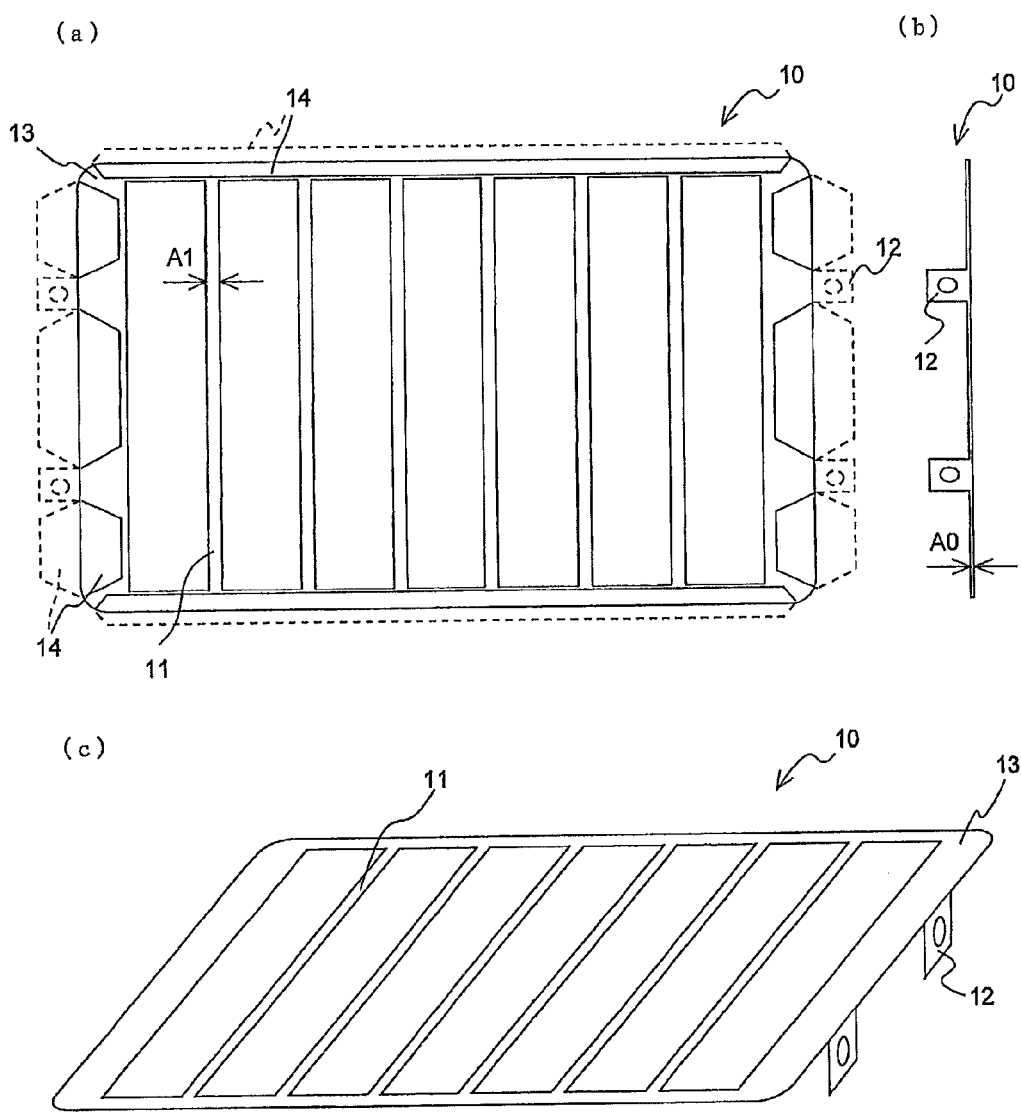
FIG. 2 includes explanatory views illustrating a structure of charging-section high-voltage electrodes according to Embodiment 1.

FIGS. 2(a), 2(b), and 2(c) are a front view, a side view, and a perspective view, respectively, illustrating the structure of the charging-section high-voltage electrodes according to Embodiment 1.

The charging-section high-voltage electrodes 11 are each shaped like a ribbon (thin plate). Alternatively, the charging-section high-voltage electrodes 11 may each be shaped like a thin wire. For example, the charging-section high-voltage electrodes 11 have a thickness A0 of about 0.05 mm to 0.5 mm and a width A1 of about 0.3 mm to 1 mm. By using a conductive thin plate, the applied voltage for starting discharge can be lowered. Such plural charging-section high-voltage electrodes 11 are arranged at intervals in a direction intersecting the airflow in the air path 61, and the plural charging-section high-voltage electrodes 11 are combined with a frame portion 13 shaped like a rectangular frame and made of a conductive material to constitute a charging-section high-voltage electrode unit 10. The shape of the frame portion 13 is not limited to the illustrated one, and an arbitrary shape can be adopted as long as the frame portion 13 connects the plural charging-section high-voltage electrodes 11 one another.

For example, the charging-section high-voltage electrode unit 10 is formed by cutting out a thin plate made of a conductive material, except for portions to become the charging-section high-voltage electrodes 11 and the frame portion 13, by press-cutting, etching, or wire machining. For example, the charging-section high-voltage electrodes 11 are made of metal such as tungsten, copper, nickel, stainless steel, zinc, or iron, an alloy mainly composed of these metals, or a material obtained by plating these metals with precious metal such as silver, gold, or platinum. By thus cutting out, from a single thin plate, the charging-section high-voltage electrode unit 10 including a combination of the charging-section high-voltage electrodes 11, assembly can be performed with ease. Instead of cutting out the single thin plate except for the portions to become the charging-section high-voltage electrodes 11 and the frame portion 13, the charging-section high-voltage electrodes 11 and the frame portion 13 can be formed as separate members, and can be combined, for example, by welding.

In Embodiment 1, the frame portion 13 shaped like a frame surrounding the outer periphery of the charging-section high-voltage electrodes 11 in the charging-section high-voltage electrode unit 10 has folded pieces 14, as shown by dashed lines in FIG. 2(a). The folded pieces 14 are folded back (hemmed). This reinforces the outer peripheral portion of the charging-section high-voltage electrode unit 10 with a small thickness, that is, the frame portion 13 of the charging-section high-voltage electrodes 11.

The frame portion 13 also has support portions 12 serving as connecting portions used to attach the charging-section high-voltage electrode unit 10 to the air-path housing 6. The support portions 12 are formed by bending tongues provided around the frame portion 13 almost at right angles. The support portions 12 have holes in which below-described insulators 7 (see FIG. 5) are to be inserted.

[Charging-Section Ground Electrode]

FIGS. 3(a), 3(b), 3(c), and 3(d) illustrate the structure of the charging-section ground electrodes according to Embodiment 1. FIG. 3(a) is a front view, FIG. 3(b) is a side view, FIG. 3(c) is a plan view, and FIG. 3(d) illustrates a processing method for the charging-section ground electrodes.

Each of the charging-section ground electrodes 21 is shaped like a flat plate, and is disposed within the air path 61 in an orientation such that a surface of the flat plate is substantially parallel to the airflow. A thickness B0 of the charging-section ground electrodes 21 is about 0.1 mm to 1.0 mm. The plural charging-section ground electrodes 21 are disposed between the charging-section high-voltage electrodes 11 such as to hold the charging-section high-voltage electrodes 11 from both sides. Therefore, the number of charging-section ground electrodes 21 corresponds to the number of charging-section high-voltage electrodes 11. The plural charging-section ground electrodes 21 are combined with a frame portion 23 made of a conductive material to constitute a charging-section ground electrode unit 20. The shape of the frame portion 23 is not limited to the illustrated one, and an arbitrary shape can be adopted as long as the frame portion 23 connects the plural charging-section ground electrodes 21.

For example, the charging-section ground electrodes 21 are formed by cutting a thin plate, which is made of a conductive material and has a thickness of about 0.1 mm to 1.0 mm, along cutting lines 22a shown by one-dot chain lines in FIG. 3(d), for example, by press cutting, etching, or wire machining and bending tongues, which are formed by cutting, by about 90 degrees along bending lines 22b shown by two-dot chain lines. By thus cutting out, from a single thin plate, the charging-section ground electrode unit 20 in which the plural charging-section ground electrodes 21 are combined, assembly can be performed with ease. Instead of cutting out the single thin plate except for the portions to become the charging-section ground electrodes 21 and the frame portion 23, the charging-section ground electrodes 21 and the frame portion 23 can be formed as separate members, and can be combined, for example, by welding.

[Charging Section]

Next, a description will be given of the charging section 1 formed by a combination of the charging-section high-voltage electrode unit 10 and the charging-section ground electrode unit 20.

FIGS. 4(a) and 4(b) are an exploded perspective view and a plan view, respectively, illustrating the structure of the charging section according to Embodiment 1. As illustrated in FIG. 4, the charging-section ground electrode unit 20 and the charging-section high-voltage electrode unit 10 are disposed such that the charging-section high-voltage electrodes 11 are inserted between the charging-section ground electrodes 21. As illustrated in FIG. 4(b) and FIG. 1, the charging-section high-voltage electrodes 11 and the charging-section ground electrodes 21 are alternately stacked in the direction intersecting the airflow in the air path 61 in a manner such as to be spaced apart from each other.

In Embodiment 1, a frame member 62 shaped like a rectangular frame is disposed between the frame portion 23 of the charging-section ground electrode unit 20 and the frame portion 13 of the charging-section high-voltage electrode unit 10. This frame member 62 serves to hold the charging-section high-voltage electrode unit 10 and the charging-section ground electrode unit 20. Also, the frame member 62 is disposed in contact with an inner wall of the air-path housing 6, and an inner wall of the frame member 62 forms a part of a wall of the air path 61. The frame portion 23 of the charging-section ground electrode unit 20 is superposed on one opening surface of the frame member 62 (opening surface on a lower side of the plane of FIG. 4(b)), and the charging-section ground electrodes 21 are inserted in the frame member 62.

As illustrated in FIGS. 1 and 4, when a virtual plane along the stacking direction of the charging-section high-voltage electrodes 11 and the charging-section ground electrodes 21 and along the direction of airflow is imagined, the cross-sectional shape of the charging-section high-voltage electrodes 11 taken along the virtual plane is shaped like a rectangle, and short sides 11a of the rectangle are opposed to the flat surfaces of the charging-section ground electrodes 21. Owing to such arrangement, the electric field intensity becomes high at four corners of the cross section of each charging-section high-voltage electrode 11, and corona discharge is to start readily. Hence, suspended particles and suspended microbes can be efficiently brought into a charged state. Further, such arrangement is effective in reducing the influence of disconnection due to electrode abrasion resulting from sputtering.

When a distance from distal ends of the short sides 11a of the charging-section high-voltage electrodes 11 to the charging-section ground electrodes 21, that is, a discharge gap length C is too short, transition to arc discharge occurs, or strong discharge occurs locally. Hence, discharge does not propagate through the entire electrodes. In contrast, when the discharge gap length C is too long, the applied voltage becomes high, and thus leakage current occurs and electric breakdown occurs in an unanticipated portion. For this reason, the discharge gap length C is preferably about 3 mm to 20 mm. In particular, to achieve stable discharge at a lower voltage, the discharge gap length C is preferably about 4 mm to 10 mm. Corona discharge is generated by applying a voltage of about +3 kV to +10 kV or about −2 kV to −10 kV from the charging high-voltage power supply 4 to the charging-section high-voltage electrodes 11 that are arranged to obtain such a discharge gap length.

Figure 6:
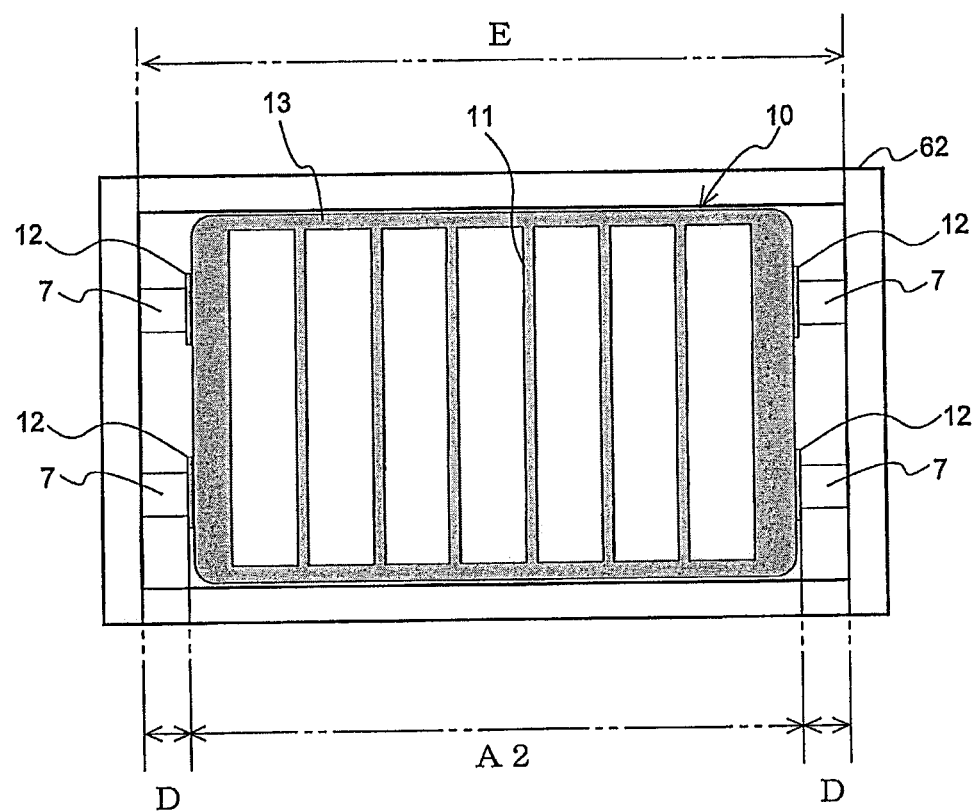
FIG. 6 illustrates a fixing manner of the charging-section high-voltage electrodes in Embodiment 1.

FIG. 5 illustrates an assembly manner of the charging-section high-voltage electrodes and the charging-section ground electrodes in Embodiment 1. FIG. 5(a) is a schematic transparent side view of a structure around the charging-section high-voltage electrodes and the charging-section ground electrodes, FIG. 5(b) is a schematic sectional view taken along line A-A' of FIG. 5(a), and FIG. 5(c) is a sectional view taken along line B-B' of FIG. 5(a) and viewed from a direction of arrows. FIG. 6 illustrates a fixing manner of the charging-section high-voltage electrodes in Embodiment 1. FIG. 6 is a front view of the charging-section high-voltage electrode unit 10 and the frame member 62, in which illustration of the charging-section ground electrode unit 20 is omitted.

As illustrated in FIGS. 5 and 6, the charging-section high-voltage electrode unit 10 is disposed on an inner side of the frame member 62 with insulators 7 being disposed therebetween. Support portions 12 are provided at both side end portions of the charging-section high-voltage electrode unit 10 in the longitudinal direction (transverse direction of the plane of FIG. 6) (see FIG. 2). The support portions 12 and the frame member 62 are connected by the insulators 7. When attaching the insulators 7, tensile force is applied. When an inside dimension in a width direction of the frame member 62 is designated as an inside dimension E, a transverse dimension of the charging-section high-voltage electrode unit 10 is designated as a transverse dimension A2, and a length of the insulators 7 is designated as a length D, the relationship among these dimensions is as follows.
(Math. 1)

$$E > (A2 + 2 \times D) \quad \text{(Math. 1)}$$

While the support portions 12 are provided at the end portions of the charging-section high-voltage electrode unit 10 in the transverse direction (longitudinal direction) in Embodiment 1, similar support portions 12 may be provided at end portions of the charging-section high-voltage electrode unit 10 in a height direction (short direction) such that the charging-section high-voltage electrode unit 10 is stretched in a vertical direction. Alternatively, the support portions 12 may be provided at the end portions of the charging-section high-voltage electrode unit 10 in both the transverse direction and the height direction such that the charging-section high-voltage electrode unit 10 is stretched in both the horizontal direction and the vertical direction.

Instead of Math. 1 described above, the following dimensional relationship may be adopted.
(Math. 2)

$$E = (A2 + 2 \times D) \quad \text{(Math. 2)}$$

When the dimensional relationship of Math. 2 is adopted, the frame member 62 itself is pulled by applying thereto a force for extending the frame member 62 outward.

By thus adopting the dimensional relationship of Math. 1, or adopting the dimensional relationship of Math. 2 and applying the outwardly extending force to the frame member 62, a force for pulling the charging-section high-voltage electrode unit 10 outward (toward the outer periphery) can be applied to the charging-section high-voltage electrode unit 10. With this configuration, the charging-section high-voltage electrodes 11 are unlikely to expand and slack when the temperature rises, fluctuations of the discharge gap length can be reduced, and stable discharge can be performed.

[Capturing Section]

Next, the capturing section 2 will be described with reference to FIG. 1. The capturing section 2 includes a plurality of capturing-section high-voltage electrodes 31 made of a conductive material and each shaped like a flat plate, and a plurality of capturing-section ground electrodes 41 similarly made of a conductive material and each shaped like a flat plate. The capturing-section high-voltage electrodes 31 and the capturing-section ground electrodes 41 are disposed within the air path 61 in an orientation such that surfaces of the flat plates are substantially parallel to the airflow and such that the capturing-section high-voltage electrodes 31 and the capturing-section ground electrodes 41 are alternately arranged in the direction orthogonal to the airflow. Electric fields are generated by applying a voltage about +1 kV to +10 kV or about −10 kV to −1 kV from the capturing high-voltage power supply 5 to the capturing-section high-voltage electrodes 31 each shaped like a flat plate. The plural capturing-section high-voltage electrodes 31 and the plural capturing-section ground electrodes 41 may each be combined into a unit by a frame, similarly to the charging-section high-voltage electrode unit 10 and the charging-section ground electrode unit 20.

[Operation]

Next, the operation of the device 100 according to Embodiment 1 will be described with reference to FIG. 1.

When the fan 3 operates, air containing suspended particles and suspended microbes flows in the air path 61, as shown by the arrows of FIG. 1. Then, when voltage is applied from the charging high-voltage power supply 4 to the charging-section high-voltage electrodes 11 via the frame portion 13, corona discharge occurs between the charging-section high-voltage electrodes 11 and the charging-section ground electrodes 21, and ions are generated by corona discharge. The generated ions adhere to the suspended particles and suspended microbes, and the suspended particles and suspended microbes are charged thereby. When voltage is applied from the capturing high-voltage power supply 5 to the capturing-section high-voltage electrodes 31, the suspended particles and suspended microbes charged in the charging section 1 are electrically captured by the capturing section 2.

In Embodiment 1, the plural charging-section high-voltage electrodes 11 each formed by a thin conductive plate are arranged at intervals, and the charging-section ground electrodes 21 each shaped like a thin plate are disposed between the charging-section high-voltage electrodes 11 such that the flat surfaces thereof are substantially parallel to the airflow in the air path 61. For this reason, the charging-section high-voltage electrodes 11 and the charging-section ground electrodes 21 are opposed to each other. By generating discharge between the charging-section high-voltage electrodes 11 and the charging-section ground electrodes 21, suspended particles and suspended microbes passing through the air path 61 can be charged. The charging-section ground electrodes 21 arranged substantially parallel to the airflow in the air path 61 serve as wind tunnels, and can induce air to discharge portions between the charging-section high-voltage electrodes 11 and the charging-section ground electrodes 21. This allows the suspended particles and suspended microbes contained in the air to be charged efficiently.

Since the plural charging-section high-voltage electrodes 11 are formed by the portions remaining after a part of the conductive flat plate is cut out, the number of components is small, easy assembly is possible, and the production cost can be reduced.

Further, since the plural charging-section ground electrodes 21 are formed by cutting and raising a part of the conductive flat plate, the number of components is small, easy assembly is possible, and the production cost can be reduced.

Embodiment 2

While the single charging-section ground electrode unit 20 is provided in Embodiment 1 described above, a description will be given of Embodiment 2 in which a plurality of charging-section ground electrode units 20 are provided. Another structure example of charging-section ground electrodes according to Embodiment 2 will be described with a focus on differences from Embodiment 1. Embodiment 2 can be combined with Embodiments described below.

Figure 7:
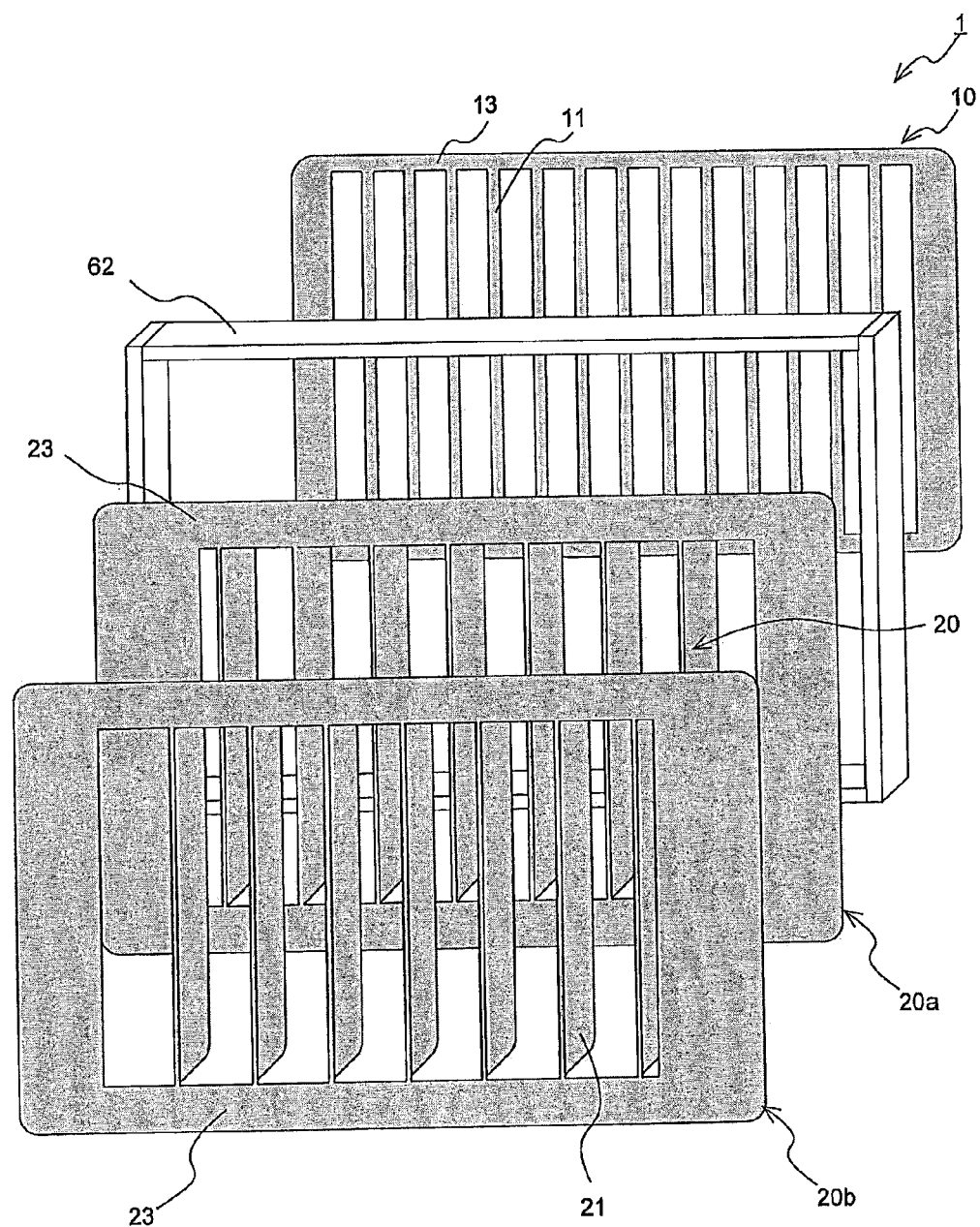
FIG. 7 is an exploded perspective view illustrating a structure of a charging section according to Embodiment 2.

FIG. 7 is an exploded perspective view illustrating a structure of a charging section according to Embodiment 2. As illustrated in FIG. 7, a charging section 1 includes two charging-section ground electrode units 20 (sometimes distinctively referred to as a charging-section ground electrode unit 20a and a charging-section ground electrode unit 20b). The charging-section ground electrode unit 20a and the charging-section ground electrode unit 20b are superposed such that charging-section ground electrodes 21 of the charging-section ground electrode unit 20b are inserted in gaps between charging-section ground electrodes 21 of the charging-section ground electrode unit 20a.

Figure 8:
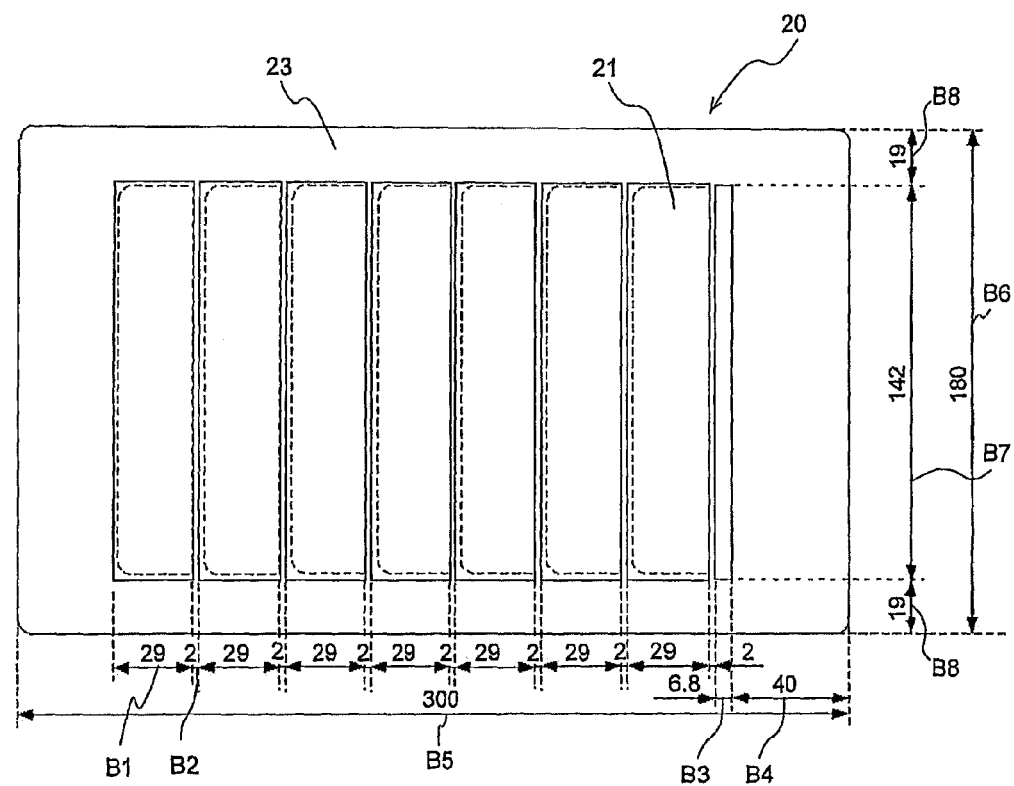
FIG. 8 illustrates exemplary dimensions of a charging-section ground electrode unit according to Embodiment 2.

FIG. 8 illustrates exemplary dimensions of the charging-section ground electrode units according to Embodiment 2.

As illustrated in FIG. 8, in the charging-section ground electrode units 20, a length B1 in an airflow direction of the charging-section ground electrodes 21 is 29 mm, and seven charging-section ground electrodes 21 are arranged at intervals of B2 (2 mm). An aperture with a width B3 (6.8 mm) is provided on a right side of the rightmost charging-section ground electrode 21 in the plane of the figure, and a portion shaped like a flat plate and having a width B4 (40 mm) is provided on a right side of the aperture. A width B5 of the charging-section ground electrode units 20 (length in a horizontal direction of the plane of FIG. 8) is 300 mm. A height B6 of the charging-section ground electrode units 20 (length in a vertical direction of the plane of FIG. 8) is 180 mm, and a height B7 of the charging-section ground electrodes 21 is 142 mm. A frame portion 23 shaped like a flat plate and having a length B8 (19 mm) is provided on upper and lower sides of the charging-section ground electrodes 21.

Figure 9:
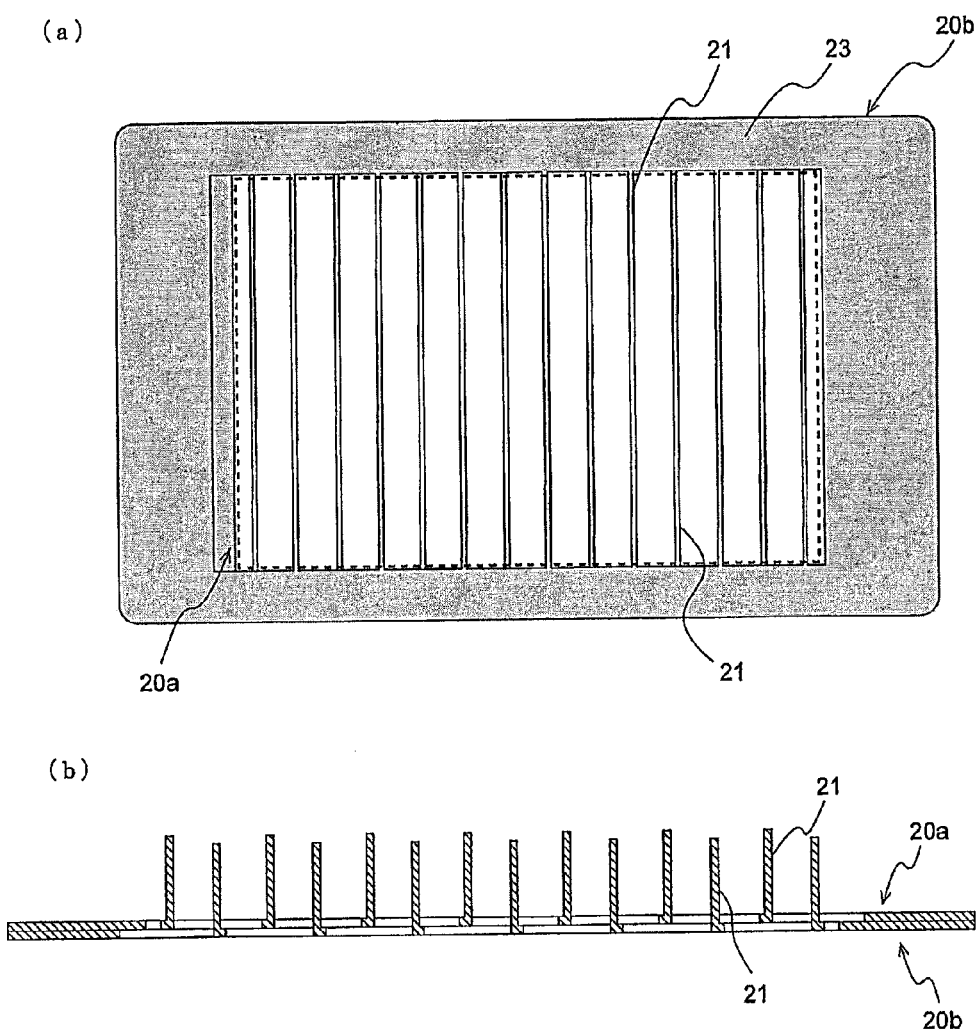
FIG. 9 illustrates a structure in which two charging-section ground electrode plates illustrated in FIG. 8 are combined.
Figure 10:
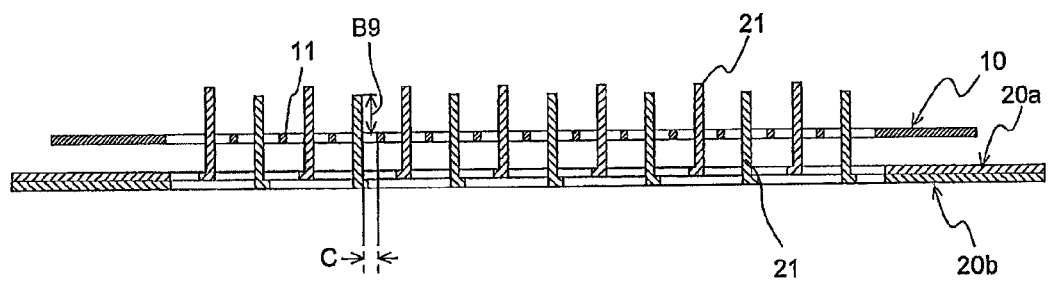
FIG. 10 is a schematic cross-sectional view illustrating an example in which the charging section of Embodiment 2 is composed of one charging-section high-voltage electrode unit and two charging-section ground electrode units.

FIG. 9 illustrates a structure in which two charging-section ground electrode units illustrated in FIG. 8 are combined. FIG. 10 is a schematic sectional view illustrating an example in which the charging section of Embodiment 2 is composed of one charging-section high-voltage electrode unit and two charging-section ground electrode units.

As illustrated in FIG. 9, two charging-section ground electrode units 20 having the same structure illustrated in FIG. 8 are superposed in a planar direction to form a plurality of charging-section ground electrodes 21. At this time, the charging-section ground electrode unit 20a and the charging-section ground electrode unit 20b are combined in a state in which the charging-section ground electrode unit 20b is turned 180 degrees relative to the charging-section ground electrode unit 20a. Then, the charging-section ground electrodes 21 of the charging-section ground electrode unit 20b are inserted in openings between the charging-section ground electrodes 21 of the charging-section ground electrode unit 20a. With this configuration, the charging-section ground electrodes 21 serving as a part of the charging-section ground electrode unit 20a and the charging-section ground electrodes 21 serving as a part of the charging-section ground electrode unit 20b are arranged alternately.

As illustrated in FIG. 10, charging-section high-voltage electrodes 11 are disposed between the charging-section ground electrodes 21 of the combined charging-section ground electrode units 20a and 20b.

A description will now be given of the reason for two charging-section ground electrode units 20 are provided in Embodiment 2.

Suspended particles and suspended microbes are charged by a collision with ion species generated in the charging section 1, and are then electrically captured by the capturing section 2, as in Embodiment 1. The direction of the electric fields in the charging section 1 is substantially parallel to the direction from the charging-section high-voltage electrodes 11 to the opposed charging-section ground electrodes 21. For this reason, the suspended particles and suspended microbes charged in the charging section can be captured by the charging-section ground electrodes 21 by increasing the length of the charging-section ground electrodes 21 toward a downstream direction of the charging-section high-voltage electrodes 11. At this time, as long as a length B9 of the charging-section ground electrodes 21 from downstream ends of the charging-section high-voltage electrodes 11 to the downstream side of the airflow (that is, length of the charging-section ground electrodes 21 on the downstream side of the discharge portions, see FIG. 10) is more than or equal to double the discharge gap length C, lines of electric force coming out of the charging-section high-voltage electrodes 11 enter the charging-section ground electrodes 21. This can enhance the capture efficiency of suspended particles and suspended microbes.

Figure 3:
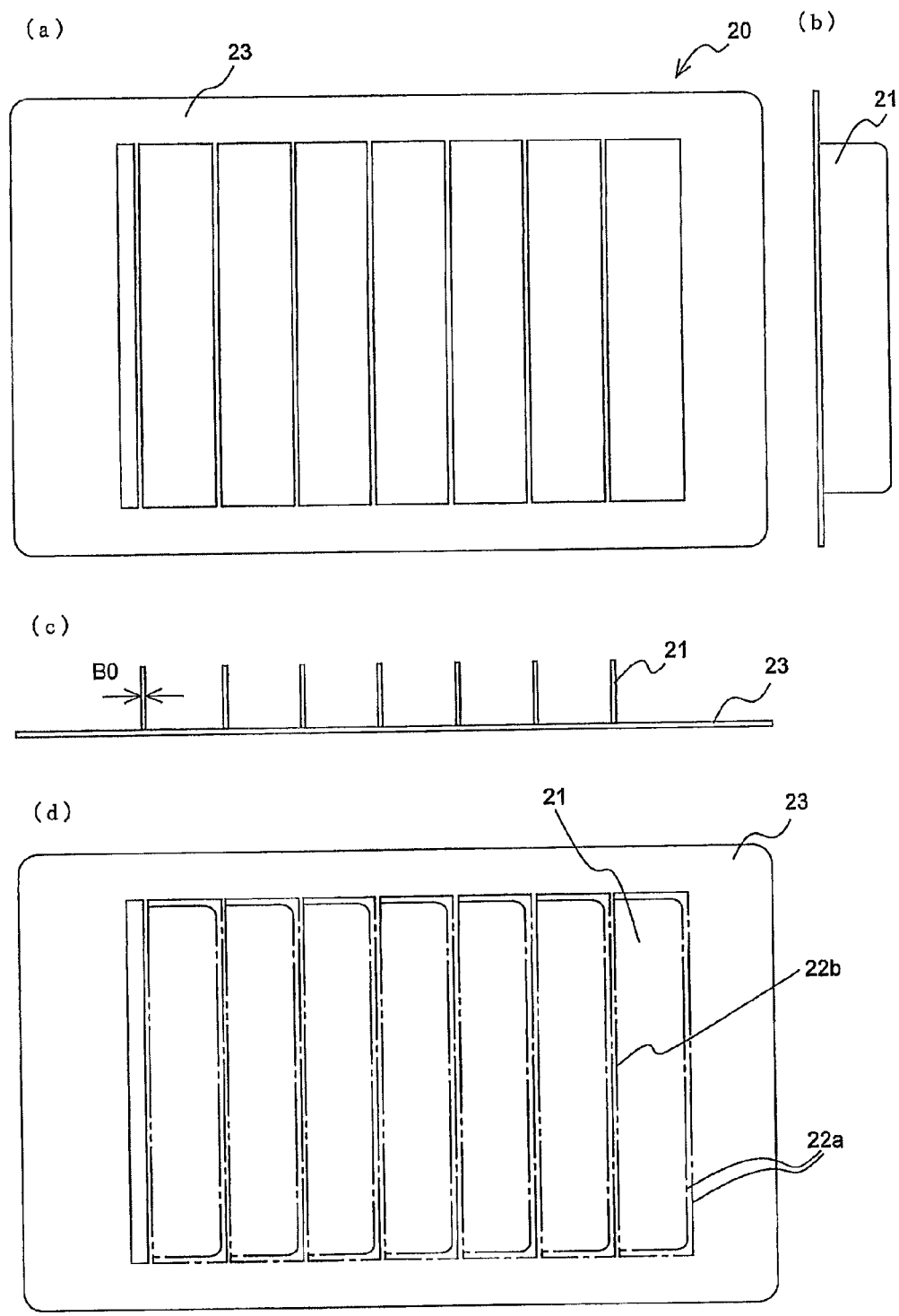
FIG. 3 includes explanatory views illustrating a structure of charging-section ground electrodes according to Embodiment 1.

However, as illustrated in FIG. 3, when the charging-section ground electrodes 21 are formed by cutting the flat plate, which forms the charging-section ground electrode unit 20, along the cutting lines 22a and bending the flat plate along the bending lines 22b, the following dimensional relationship holds.

(Math. 3)

$$B1 = 2 \times C + A1$$

where B1: length of charging-section ground electrodes 21, C: discharge gap length, A1: width of charging-section high-voltage electrodes 11.

Since the downstream length B9 of the charging-section ground electrodes 21 is shorter than the length B1 of the charging-section ground electrodes 21, if the charging-section high-voltage electrodes 11 are to be inserted in all the gaps between the charging-section ground electrodes 21 of the charging-section ground electrode unit 20 formed by a single flat plate, the length B1 of the charging-section ground electrodes 21 cannot be made more than or equal to double the discharge gap length C.

Accordingly, in Embodiment 2, two charging-section ground electrode units 20 having a similar structure are provided. When two charging-section ground electrode units 20 are provided in this way, the number of charging-section ground electrodes 21 becomes double the number of FIG. 3. As illustrated in FIG. 10, the charging-section high-voltage electrodes 11 are disposed in the gaps formed between the charging-section ground electrodes 21 of the two charging-section ground electrode units 20. With this configuration, a number of charging-section high-voltage electrodes 11, which is double the number of FIG. 3, can be formed in the charging-section high-voltage electrode unit 10. According to the structure of FIG. 10, the length B9 of the charging-section ground electrodes 21 on the downstream side of the discharge portions can be made more than or equal to double the discharge gap length C by adjusting the width A1 of the charging-section high-voltage electrodes 11.

By superposing the two charging-section ground electrode units 20 with the similar structure in orientations shifted 180 degrees, the discharge gap length C can be constantly set at regular intervals. Further, since the charging-section ground electrode units 20 with the similar structure are used, the increase in production cost of the components can be suppressed.

When a projection plane of an aperture formed by combining the charging-section ground electrode unit 20a and the charging-section ground electrode unit 20b (shown by a dashed line in FIG. 9(*a*)) is set to be equal to a projection plane of the entire discharge region between the charging-section high-voltage electrodes 11 and the charging-section ground electrodes 21, the discharge region is disposed on all channels of air passing through the aperture formed by the charging-section ground electrode unit 20a and the charging-section ground electrode unit 20b, that is, air passing through the air path 61 of the device 100. With this configuration, it is possible to charge more suspended particles and suspended microbes contained in the air passing through the device 100 and to enhance the capture efficiency of the suspended particles and suspended microbes.

In this way, in Embodiment 2, suspended particles and suspended microbes can be captured by the charging-section ground electrodes 21 of the charging section 1. Hence, the capturing section 2 can be omitted. When the capturing section 2 is omitted, the capture efficiency of the suspended particles and suspended microbes becomes lower than in Embodiment 1 including the capturing section 2, but the number of components of the device 100 can be reduced.

While two charging-section ground electrode units 20 are provided in Embodiment 2, the number of charging-section ground electrode units 20 is not limited to two, and may be three or more. The number of charging-section ground electrode units 20 can be appropriately set in consideration of, for example, the length of the charging-section ground electrodes 21 in the airflow direction, the width of the air path 61, and the discharge gap length.

Embodiment 3

Embodiment 3 will be described with a focus on differences of another exemplary structure of a charging section from that adopted in Embodiment 1. Embodiment 3 can be combined with Embodiments described below.

Figure 11:
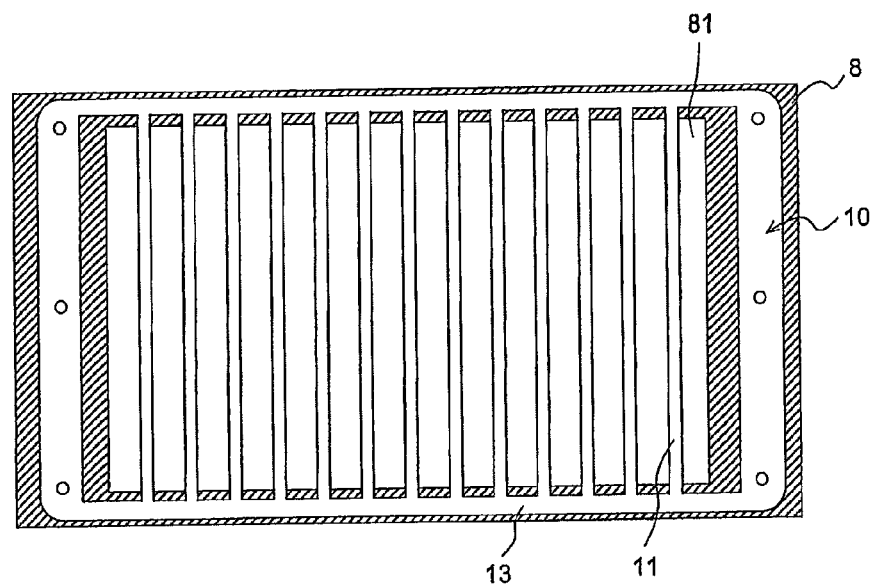
FIG. 11 is a rear view of a charging-section high-voltage electrode unit according to Embodiment 3.

FIG. 11 is a rear view of a charging-section high-voltage electrode unit according to Embodiment 3.

In Embodiment 1 illustrated in FIG. 6, the support portions 12 provided on the charging-section high-voltage electrode unit 10 are attached to the frame member 62 with the insulators 7 being disposed therebetween. In Embodiment 3, a charging-section high-voltage electrode unit 10 is assembled without forming support portions 12 and insulators 7. As illustrated in FIG. 11, the charging-section high-voltage electrode unit 10 is attached to be superposed on an insulating body 8 shaped like a frame-shaped rectangular flat plate. The width and height dimensions of the rectangular frame shape of the insulating body 8 are large enough to include a frame portion 13 of the charging-section high-voltage electrode unit 10, and the charging-section high-voltage electrode unit 10 can be superposed on the insulating body 8 such that the frame portion 13 does not protrude from the insulating body 8. The charging-section high-voltage electrode unit 10 and the insulating body 8 are screwed at both longitudinal end portions with unillustrated screws. Instead of screwing, claws provided on the insulating body 8 may be caught in holes provided in the charging-section high-voltage electrode unit 10. This further facilitates assembly. By thus superposing the frame portion 13 of the charging-section high-voltage electrode unit 10 on the insulating body 8, the charging-section high-voltage electrode unit 10 shaped like a thin plate can be reinforced.

Figure 12:
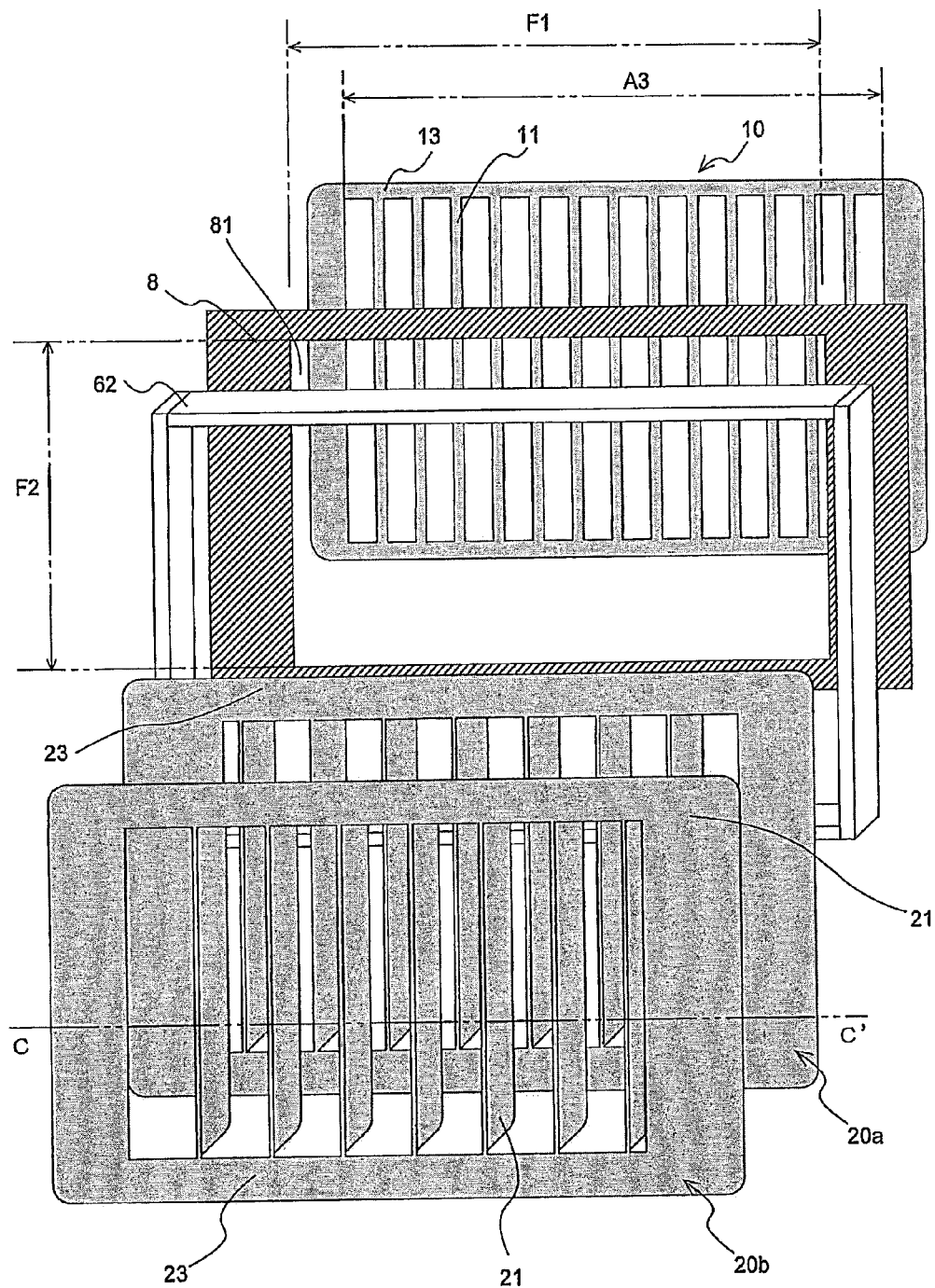
FIG. 12 is an exploded perspective view of a charging section according to Embodiment 3.

FIG. 12 is an exploded perspective view of the charging section according to Embodiment 3.

As illustrated in FIG. 12, the charging-section high-voltage electrode unit 10 is attached to one opening surface of a frame member 62 with the insulating body 8 being disposed therebetween. Charging-section ground electrode units 20 are attached to an opposite opening surface of the frame member 62. While two charging-section ground electrode units 20 are combined in FIG. 12, as described in conjunction with Embodiment 2, a single charging-section ground electrode unit 20 may be provided as in Embodiment 1. Charging-section ground electrodes 21 of the charging-section ground electrode units 20 are inserted between a plurality of charging-section high-voltage electrodes 11 that are arranged at predetermined intervals.

Figure 13:
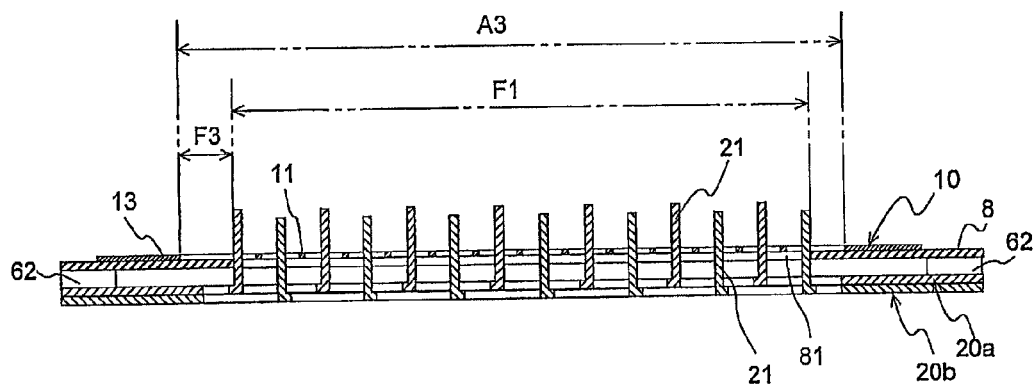
FIG. 13 is a schematic sectional view of the charging section of Embodiment 3.

FIG. 13 is a schematic sectional view of the charging section according to Embodiment 3. FIG. 13 is a cross-sectional view taken along line C-C' of FIG. 12 and illustrates an assembled state of the charging section 1 of FIG. 12.

As illustrated in FIG. 13, the insulating body 8 and the charging-section high-voltage electrode unit 10 are disposed on an upper side of the frame member 62 in the plane of FIG. 13, and two charging-section ground electrode units 20 are superposed on a lower side of the frame member 62 in the plane of FIG. 13. The insulating body 8 is interposed between the charging-section high-voltage electrode unit 10 and the charging-section ground electrode units 20, and the charging-section high-voltage electrode unit 10 and the charging-section ground electrode units 20 are not directly placed one on the other.

As illustrated in FIG. 12, a height F2 of a substantially rectangular aperture 81 provided in almost the center of the insulating body 8 shaped like a rectangular frame is substantially equal to a height B7 of the charging-section ground electrodes 21. The plural charging-section ground electrodes 21 are inserted in the aperture 81, and the charging-section high-voltage electrodes 11 are disposed between the charging-section ground electrodes 21. Therefore, discharge portions formed between the charging-section ground electrodes 21 and the charging-section high-voltage electrodes 11 fit within a width F1 of the aperture 81. As illustrated in FIG. 13, the endmost charging-section ground electrodes 21 are in contact with both right and left end portions of the aperture 81, and there is little gap between the endmost charging-section ground electrodes 21 and the end portions of the aperture 81. The charging-section ground electrodes 21 disposed on both right and left ends function as side walls of an air path 61. Owing to such a structure, the insulating body 8 prevents air from leaking to portions other than the discharge portions formed between the charging-section ground electrodes 21 and the charging-section high-voltage electrodes 11, and air sent by a fan 3 passes through any of the discharge portions. Therefore, suspended particles and suspended microbes in the air can be efficiently charged by the charging section 1.

As illustrated in FIG. 13, an inner width A3 of a frame portion 13 of the charging-section high-voltage electrode unit 10 is larger than the width F1 of the aperture 81 of the insulating body 8, and the insulating body 8 extends over a width F3 between the frame portion 13 of the charging-section high-voltage electrode unit 10 and the charging-section ground electrodes 21. For this reason, lines of electric force from the frame portion 13, which do not contribute to corona discharge, in the charging-section high-voltage electrodes 11, can be removed, and this increases the electric field intensity at the discharge portions. Since the electric field intensity at the discharge portions increases, corona discharge can be started at low voltage.

Front and rear surfaces of the ribbon-shaped charging-section high-voltage electrodes 11 (surfaces on long sides of the charging-section high-voltage electrodes 11 illustrated in FIG. 13, which are not opposed to the charging-section ground electrodes 21) may be covered with an insulating material. This can remove extra lines of electric force that do not contribute to corona discharge, and improves safety from high voltage.

Figure 14:
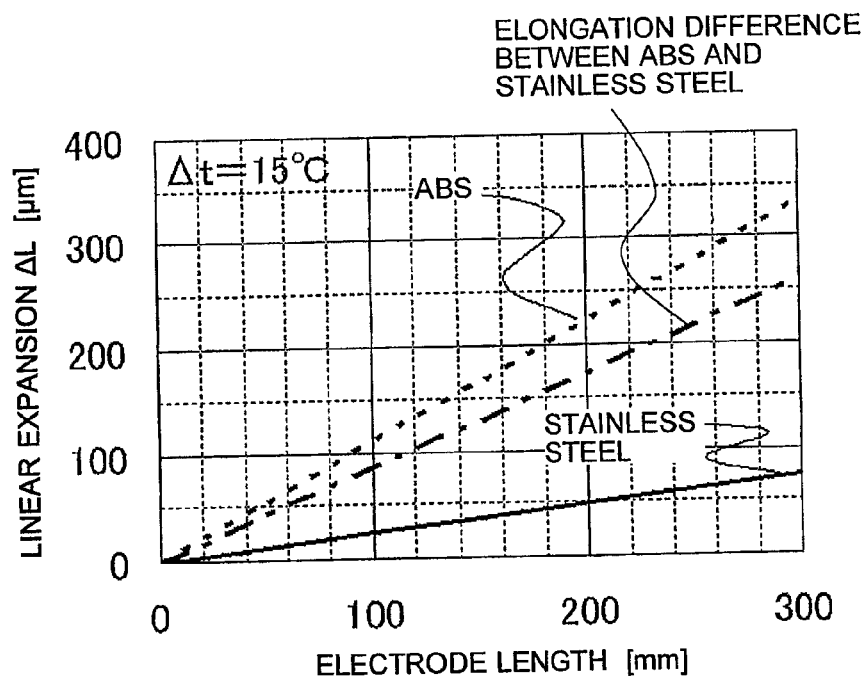
FIG. 14 is a graph showing linear expansions of stainless steel and ABS and the difference therebetween when the temperature is 15 degrees C. higher than during production.

The charging-section high-voltage electrode unit 10 and the insulating body 8 may be coagulated with thermosetting resin. With this configuration, when the temperature increases and the charging-section high-voltage electrode unit 10 made of metal expands, the thermosetting resin sets. Hence, when the temperature decreases after setting, a force is applied in a direction of contraction. This can suppress the change in discharge gap length due to the temperature rise. When the temperature during production is set at a room temperature of 20 to 25 degrees C., the temperature differs up to about 15 degrees C. depending on the usage environment. For this reason, if linear expansion occurs to the charging-section high-voltage electrodes 11, slack may occur. FIG. 14 is a graph showing linear expansions of stainless steel and ABS and the difference therebetween when the temperature is 15 degrees C. higher than during production. In general, since the amount of elongation of a resin material in accordance with the temperature is more than that of a metal material, the metal is pulled by the resin. When the insulating body 8 is formed by a plate having a thickness of 1 mm or more, the slack due to the temperature change can be taken out of the charging-section high-voltage electrodes 11.

Embodiment 4

As described above in conjunction with Embodiment 1, the charging-section high-voltage electrodes 11 are each formed by a thin conductive plate. With this configuration, the discharge start voltage can be lowered, but the charging-section high-voltage electrodes 11 are liable to be shaken by the wind depending on the thickness thereof. When the charging-section high-voltage electrodes 11 shake, the discharge gap length changes, and this makes discharge unstable. Accordingly, Embodiment 4 adopts a structure for suppressing the shake of the charging-section high-voltage electrodes 11 due to the wind. Embodiment 4 will be described with a focus on differences from Embodiment 1. Embodiment 4 can also be combined with Embodiments described below.

FIG. 15 illustrates charging-section high-voltage electrodes and charging-section ground electrodes according to Embodiment 4. FIG. 15 illustrates a pair of charging-section ground electrodes 21 and a charging-section high-voltage electrode 11 disposed therebetween. In FIGS. 15(a) and 15(b), upper side views are principal plan views and lower side views are principal front views.

As illustrated in FIGS. 15(a) and 15(b), spacers 9 are provided to bridge the charging-section high-voltage electrode 11 and the charging-section ground electrodes 21 on both sides of the charging-section high-voltage electrode 11 and to fix the position of the charging-section high-voltage electrode 11. In consideration of the likelihood of the charging-section high-voltage electrode 11 shaking owing to the wind, one or a plurality of spacers 9 can be provided in a height direction of the charging-section high-voltage electrode 11. The spacers 9 are made of a material that has little influence on discharge. By forming such spacers 9, the position of the charging-section high-voltage electrode 11 is fixed, and fluctuations of the discharge gap length are suppressed. Hence, stable discharge can be carried out continuously.

As illustrated in FIG. 15(a), the spacers 9 may be rod-shaped (linear). This allows the spacers 9 to be produced easily.

Alternatively, as illustrated in FIG. 15(b), the spacers 9 may be arc-shaped to increase the creepage distance between the charging-section high-voltage electrode 11 and the charging-section ground electrodes 21. By thus increasing the creepage distance between the charging-section high-voltage electrode 11 and the charging-section ground electrodes 21, creeping discharge can be suppressed.

In the case of combination with the insulating body 8 described with reference to FIG. 11 and so on, the spacers 9 may be attached to the insulating body 8, or the insulating body 8 and the spacers 9 may be formed integrally.

Embodiment 5

A modification of charging-section high-voltage electrodes according to Embodiment 5 will be described with a focus on differences from Embodiment 1. Embodiment 5 can be combined with other Embodiments described below.

Figure 16:
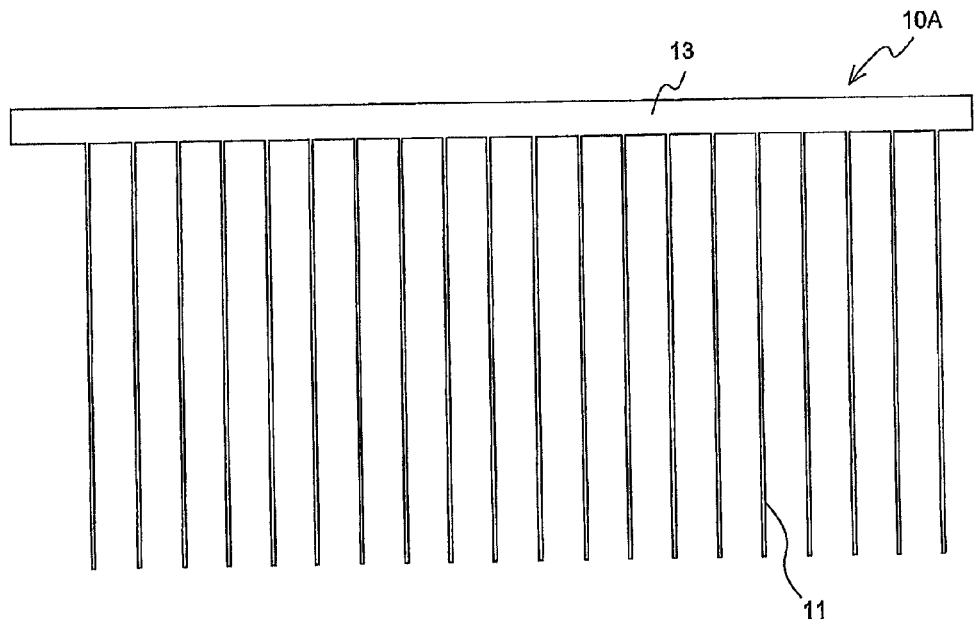
FIG. 16 illustrates charging-section high-voltage electrodes according to Embodiment 5.
Figure 17:
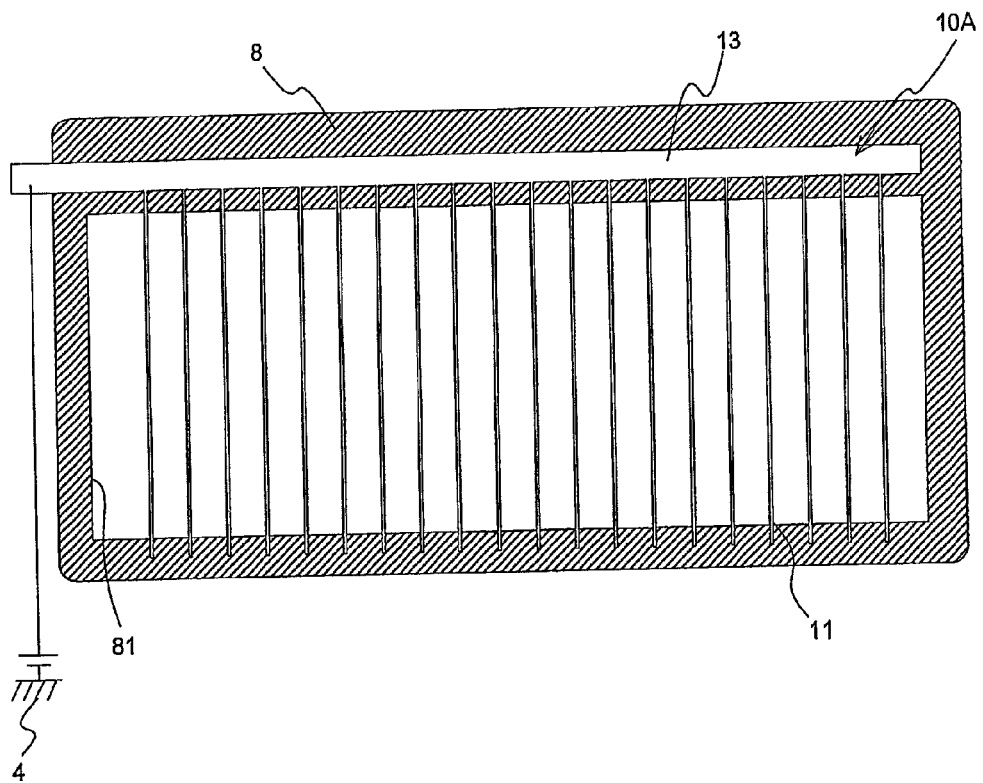
FIG. 17 illustrates a state in which an insulating body is combined with the charging-section high-voltage electrodes of Embodiment 5.

FIG. 16 illustrates charging-section high-voltage electrodes according to Embodiment 5. FIG. 17 illustrates a state in which an insulating body is combined with the charging-section high-voltage electrodes of Embodiment 5.

In Embodiment 1 described above, as illustrated in FIG. 2, the charging-section high-voltage electrode unit 10 is formed by cutting out a thin plate made of a conductive material in a rectangular form such that the charging-section high-voltage electrodes 11 remain.

In contrast, in Embodiment 5, as illustrated in FIG. 16, a charging-section high-voltage electrode unit 10A, in which a plurality of charging-section high-voltage electrodes 11 are combined, is formed by processing a thin plate made of a conductive material into a comb shape. In the charging-section high-voltage electrode unit 10A, the plural charging-section high-voltage electrodes 11 extend from a frame portion 13, which extends in a width direction of an air path 61, in a direction orthogonal to the frame portion 13 (corresponding to a height direction of the air path 61). The charging-section high-voltage electrodes 11 are each open at one end without being connected to another member. Such charging-section high-voltage electrodes 11 are formed by processing a thin plate made of a conductive material, by, for example, press cutting, wire machining, or etching.

A charging high-voltage power supply 4 is connected to the frame portion 13 of the charging-section high-voltage electrode unit 10A. The frame portion 13 functions as a unit for feeding power to the plural charging-section high-voltage electrodes 11, and the plural charging-section high-voltage electrodes 11 are kept at almost the same potential.

By clamping the charging-section high-voltage electrode unit 10A between two insulating bodies 8 of the same shape from front and rear sides (front and rear sides in a direction of an airflow) or by placing the charging-section high-voltage electrode unit 10A in a mold and pouring insulating resin into the mold, the charging-section high-voltage electrode unit 10A and the insulating bodies 8 are combined. As illustrated in FIG. 17, the comb-shaped charging-section high-voltage electrode unit 10A is superposed on each insulating body 8 such that the charging-section high-voltage electrodes 11 serving as comb teeth extend from one side (upper side in the plane of the figure) of the rectangular frame-shaped insulating body 8 to the other side (lower side in the plane of the figure). In the charging-section high-voltage electrode unit 10A, the frame portion 13 serving as a grip of the comb is placed on the insulating body 8. By combining the charging-section high-voltage electrodes 11 and the insulating material, abnormal discharge between the charging-section high-voltage electrodes 11 and their surroundings can be prevented. By connecting one end of each of the charging-section high-voltage electrodes 11 to the frame portion 13 and freeing the other end thereof, each of the plural charging-section high-voltage electrodes 11 can be fixed at the other end to the insulating body 8. Since the charging-section high-voltage electrodes 11 are laid in a tensioned state, they can be stretched without any slack even when the rigidity of the frame portion 13 is low.

The combination of the charging-section high-voltage electrode unit 10A and the insulating bodies 8 is disposed within the air path 61. At this time, the insulating bodies 8 are fitted in a peripheral wall of the air path 61, and peripheral walls of apertures 81 of the insulating bodies 8 form a part of a wind tunnel. By thus assembling the combination of the charging-section high-voltage electrode unit 10A and the insulating bodies 8 in the air path 61, assembly can be performed with ease.

Embodiment 6

A modification of charging-section high-voltage electrodes according to Embodiment 6 will be described. Embodiment 6 will be described with a focus on differences from Embodiment 5.

Figure 18:
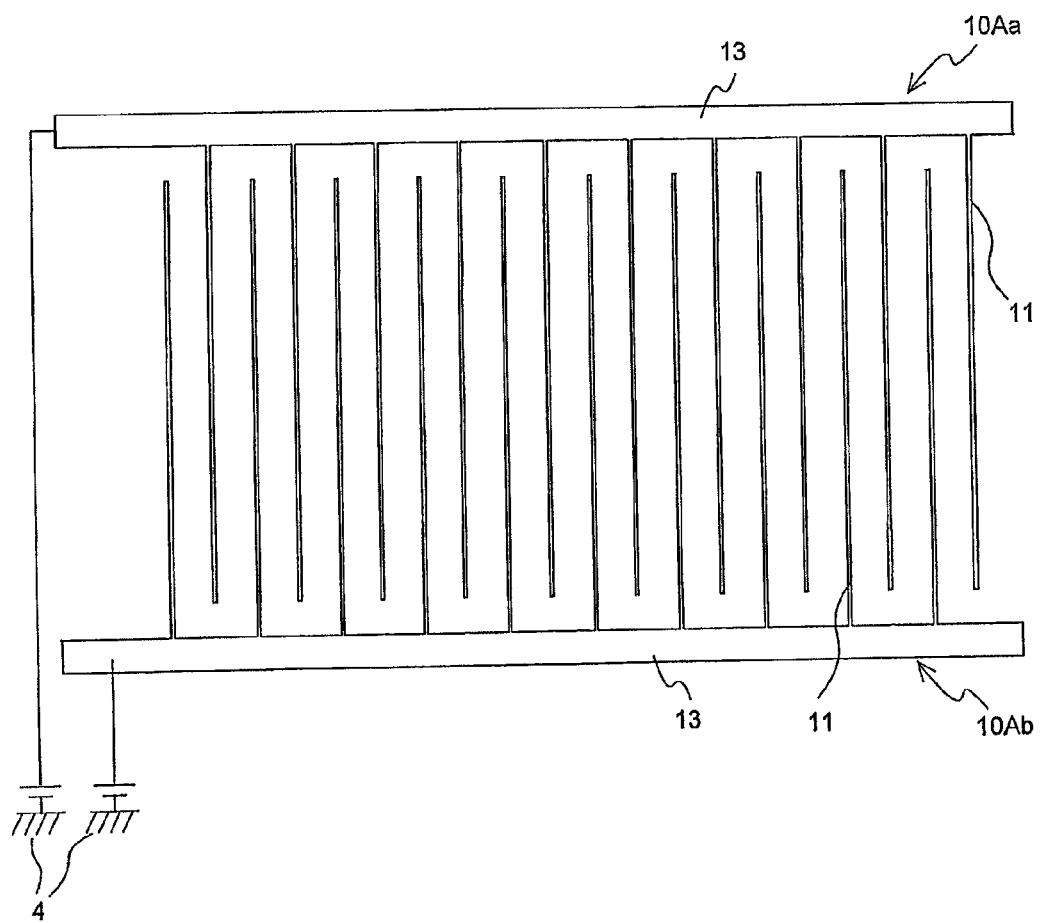
FIG. 18 illustrates charging-section high-voltage electrodes according to Embodiment 6.
Figure 19:
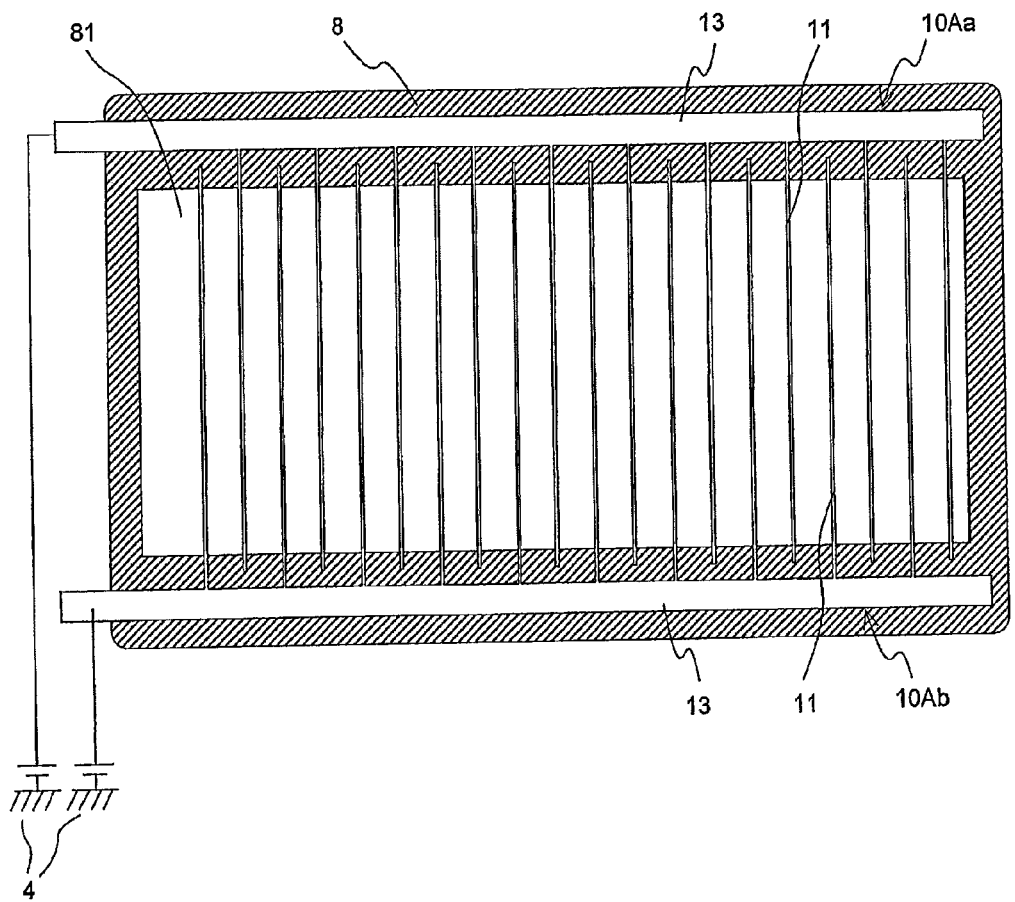
FIG. 19 illustrates a state in which an insulating body is combined with the charging-section high-voltage electrodes of Embodiment 6.

FIG. 18 illustrates charging-section high-voltage electrodes according to Embodiment 6. FIG. 19 illustrates a state in which an insulating body is combined with the charging-section high-voltage electrodes of Embodiment 6.

In the comb-shaped charging-section high-voltage electrode unit 10A of Embodiment 5 described above, one end of each of the charging-section high-voltage electrodes 11 is a free end.

In Embodiment 6, as illustrated in FIG. 18, two charging-section high-voltage electrode units 10A, which are comb-shaped similarly to Embodiment 5, are arranged to be opposed to each other such that charging-section high-voltage electrodes 11 point in alternate opposite directions. For convenience, two charging-section high-voltage electrode units 10A are sometimes distinctively referred to as charging-section high-voltage electrode units 10Aa and 10Ab. As illustrated in FIG. 18, the charging-section high-voltage electrode unit 10Aa and the charging-section high-voltage electrode unit 10Ab are arranged in a horizontally symmetric position in the plane of the figure. Charging high-voltage power supplies 4 are connected to frame portions 13 of the charging-section high-voltage electrode units 10Aa and 10Ab, and the frame portions 13 of the charging-section high-voltage electrode units 10Aa and 10Ab function as power feed units. As illustrated in FIG. 19, the two charging-section high-voltage electrode units 10A are combined with an insulating body 8, similarly to Embodiment 5.

Since the units for feeding power to the charging section 1 are disposed at two separate positions, for example, even when continuity of one of the power feed lines is lost by disconnection, suspended particles and suspended microbes in the air can be charged by power supplied from the other power feed line. Therefore, remarkable degradation of dust collection performance can be suppressed even in an unexpected situation such as disconnection.

Embodiment 7

A modification of charging-section high-voltage electrodes according to Embodiment 7 will be described. In Embodiments 1 to 6 described above, the charging-section high-voltage electrode unit in which the plural charging-section high-voltage electrodes are combined is formed by, for example, subjecting a thin conductive plate to cutting out such that the charging-section high-voltage electrodes remain. In Embodiment 7, a plurality of charging-section high-voltage electrodes that are produced separately are combined.

Figure 20:
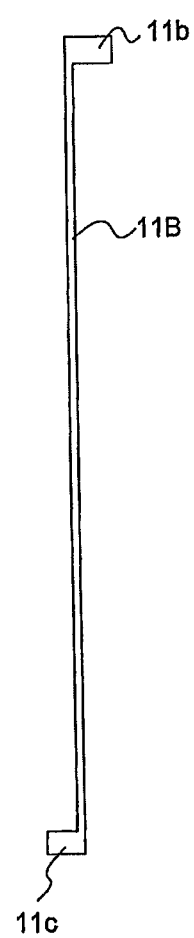
FIG. 20 illustrates a charging-section high-voltage electrode according to Embodiment 7.

FIG. 20 illustrates a charging-section high-voltage electrode according to Embodiment 7.

As illustrated in FIG. 20, in a charging-section high-voltage electrode 11B of Embodiment 7, a connecting portion 11b and a connecting portion 11c continue from both end portions of a ribbon-shaped portion (thin-plate portion) similar to those adopted in Embodiments 1 to 3 such as to extend in a direction intersecting the ribbon-shaped portion. The charging-section high-voltage electrode 11B is hook-shaped as a whole.

A production method for the charging-section high-voltage electrode 11B is similar to those adopted in Embodiments described above. The charging-section high-voltage electrode 11B can be produced by cutting out a thin conductive plate, for example, by press cutting, etching, or wire machining.

Figure 22:
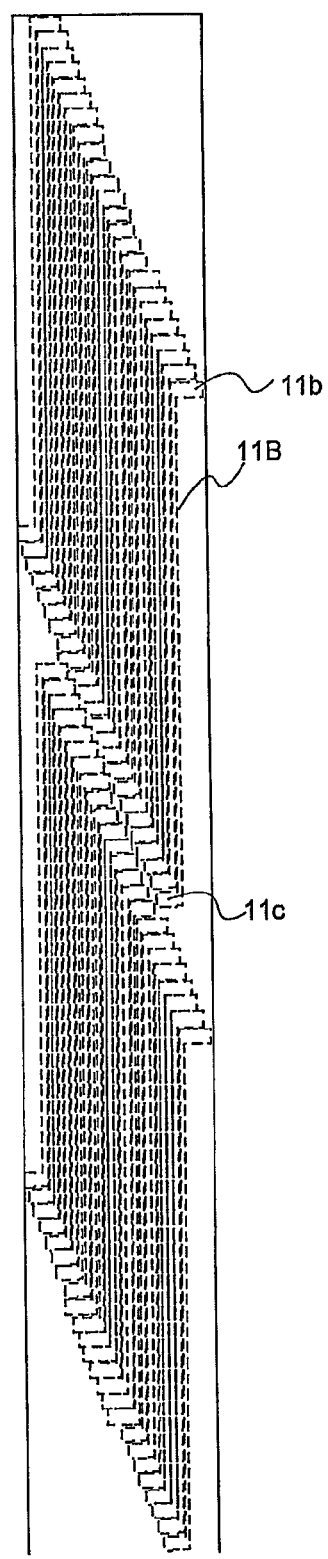
FIG. 22 illustrates an exemplary arrangement in a case in which charging-section high-voltage electrodes of Embodiment 7 are cut out of a single plate.

FIGS. 21 and 22 illustrate exemplary arrangements for cutting charging-section high-voltage electrodes of Embodiment 7 out of a single plate. For example, as illustrated in FIGS. 21 and 22, hook-shaped charging-section high-voltage electrodes 11B of Embodiment 7 are cut out of a single thin conductive plate. Multiple charging-section high-voltage electrodes 11B can be formed from a single thin plate without any waste by devising the arrangement when cutting out the charging-section high-voltage electrodes 11B.

Figure 23:
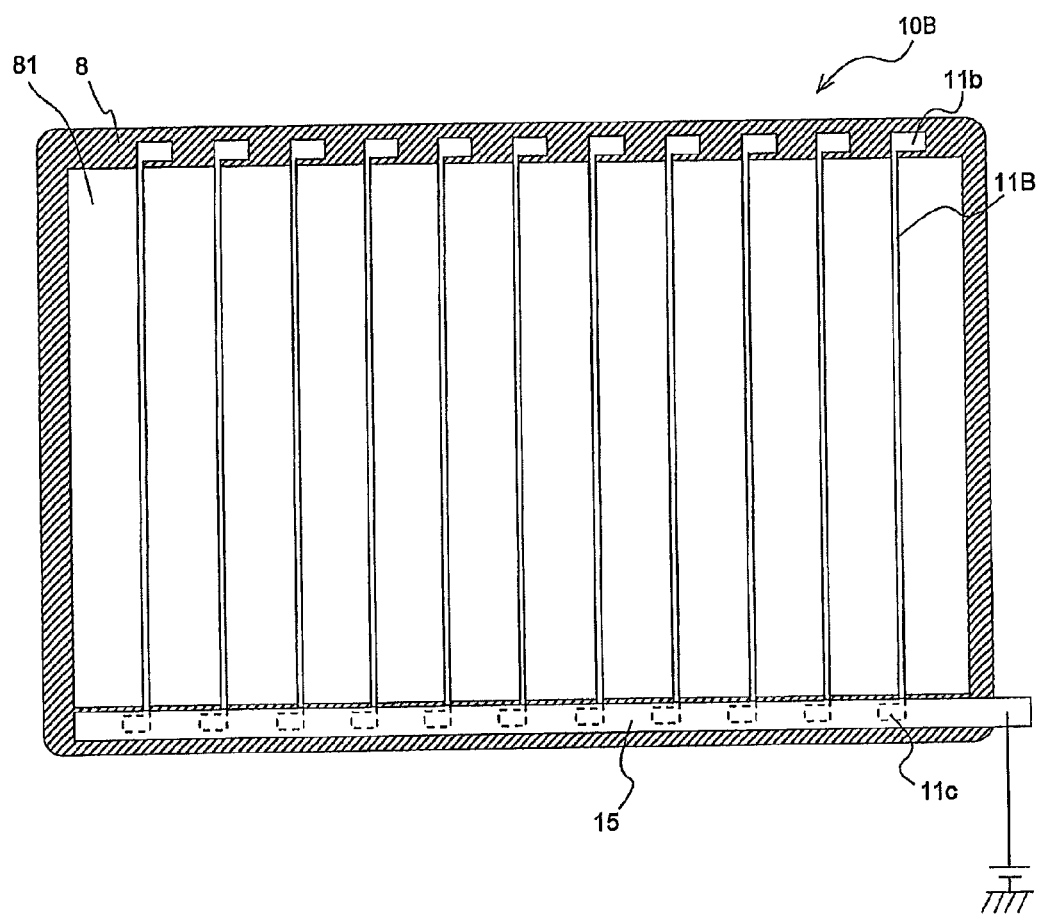
FIG. 23 illustrates a state in which the charging-section high-voltage electrodes of Embodiment 7 are combined with an insulating body.

FIG. 23 illustrates a state in which the charging-section high-voltage electrodes and an insulating body according to Embodiment 7 are combined. As illustrated in FIG. 23, a plurality of charging-section high-voltage electrodes 11B are arranged at regular intervals on an insulating body 8 shaped like a rectangular frame. At this time, the charging-section high-voltage electrodes 11B are disposed on an aperture 81 of the insulating body 8, and connecting portions 11b and connecting portions 11c are disposed on the insulating body 8 with the aperture 81 being disposed therebetween. A power feed plate 15 electrically connected to a charging high-voltage power supply 4 is placed on the connecting portions 11c. In this way, in Embodiment 7, the insulating body 8 functions as a frame that combines the plural charging-section high-voltage electrodes 11 (corresponding to the frame portion 13 in Embodiments 1 to 6), and the insulating body 8 and the plural charging-section high-voltage electrodes 11 constitute a charging-section high-voltage electrode unit 10B.

Voltage is applied from the charging high-voltage power supply 4 via the power feed plate 15 to the charging-section high-voltage electrodes 11B. When the voltage is applied from the charging high-voltage power supply 4, the applied voltage and the charging-section high-voltage electrodes 11B have the same potential.

FIG. 24 illustrates the structure of portions of the charging-section high-voltage electrodes assembled to the insulating body in Embodiment 7. FIGS. 24(a) and 24(b) are a front view and a schematic sectional view, respectively, of portions near the connecting portions 11c each provided at one end of the corresponding charging-section high-voltage electrode 11B. As illustrated in FIG. 24, a surface of the insulating body 8 has grooves 82 in which the connecting portions 11c of the charging-section high-voltage electrodes 11B are to be fitted. The charging-section high-voltage electrode unit 10B is formed by fitting the connecting portions 11c in the grooves 82 of the insulating body 8, placing the power feed plate 15 on the insulating body 8, and covering these elements with the insulating body 8. While FIG. 24 illustrates only the assembled portions of the connecting portions 11c and the insulating body 8, this structure also applies to the connecting portions 11b. With this configuration, the charging-section high-voltage electrodes 11B are assembled to the insulating body 8 without being displaced. This enhances assembly accuracy of products, and facilitates assembly operation. Instead of combining the plate-shaped insulating body 8 and the charging-section high-voltage electrodes 11B, insulating resin poured around the charging-section high-voltage electrodes 11B may be applied. This provides similar advantages.

Embodiment 8

In Embodiment 1 described above, the discharge electrodes (charging-section high-voltage electrodes 11, capturing-section high-voltage electrodes 31) of the charging section 1 and the capturing section 2 are provided with the respective ground electrodes (charging-section ground electrodes 21, capturing-section ground electrodes 41). As Embodiment 8, a corona discharge device (hereinafter referred to as a device 100) in which a charging section 1 and a capturing section 2 share ground electrodes will be described. Embodiment 8 will be described with a focus on differences from Embodiment 1.

Figure 25:
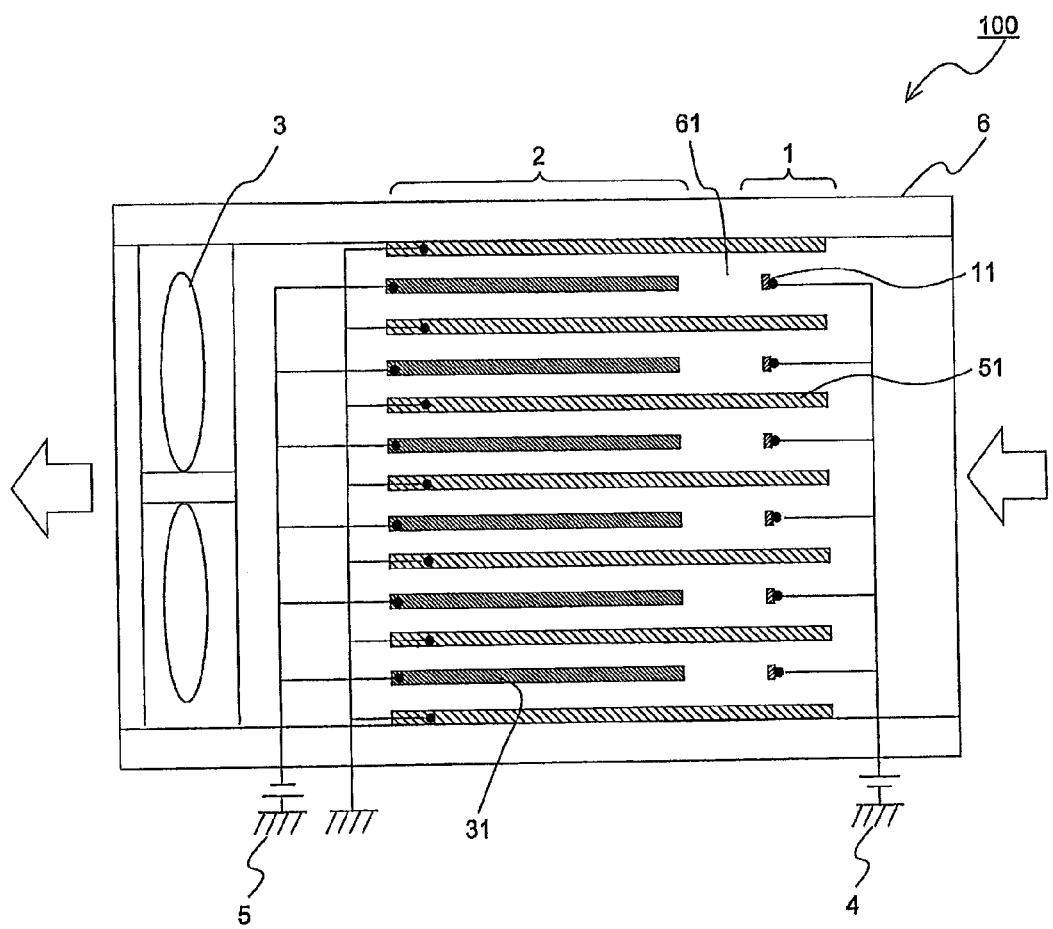
FIG. 25 is a schematic view of an electric dust collection device utilizing corona discharge electrodes according to Embodiment 8.

FIG. 25 is a schematic view of an electric dust collection device utilizing corona discharge electrodes according to Embodiments 8. The device 100 includes ground electrodes 51 shared by the charging section 1 and the capturing section 2. The ground electrodes 51 are shaped like substantially flat plates, and are arranged in an air path 61 such that surfaces of the flat plates are substantially parallel to an airflow direction. Within the air path 61, the plural ground electrodes 51 are disposed at predetermined intervals. In gaps between the ground electrodes 51, charging-section high-voltage electrodes 11 and capturing-section high-voltage electrodes 31 are disposed. In the airflow direction, the charging-section high-voltage electrodes 11 are disposed on an upstream side, and the capturing-section high-voltage electrodes 31 are disposed on a downstream side.

Figure 26:
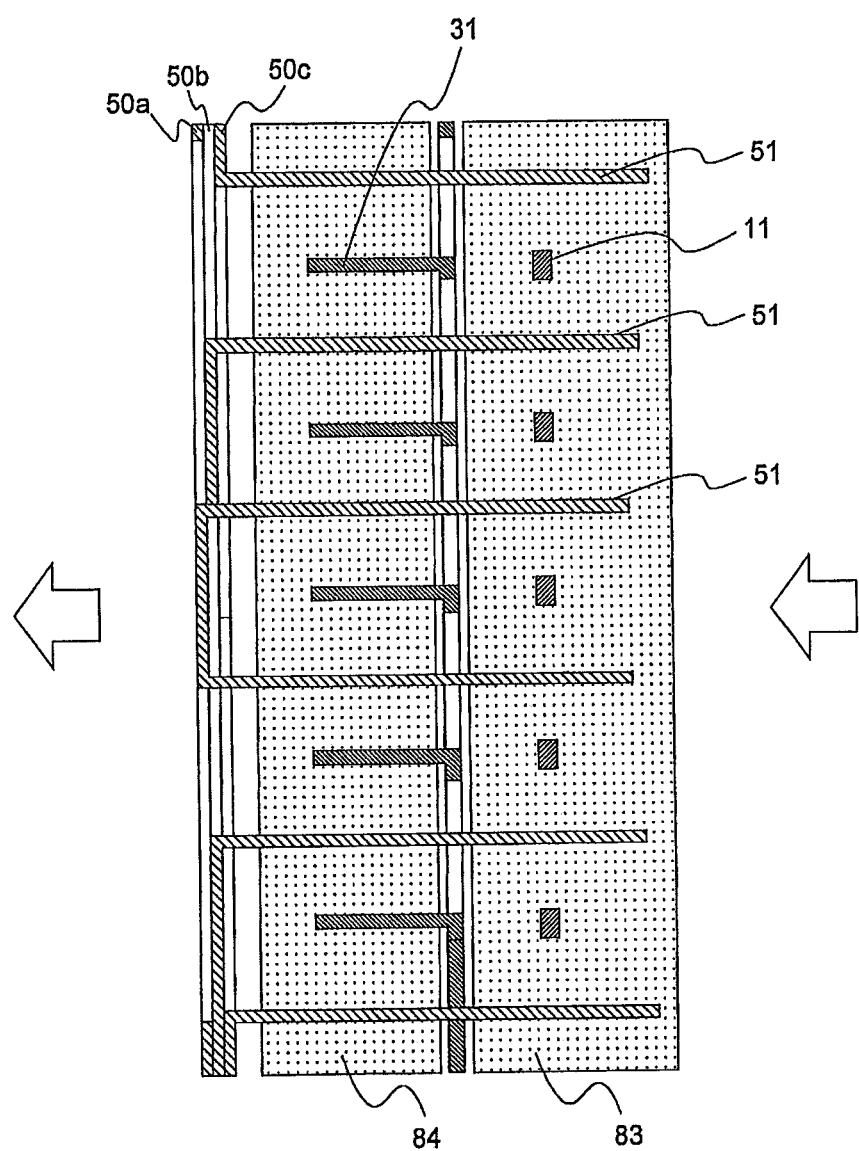
FIG. 26 is a principal schematic sectional view illustrating structures of a charging section and a capturing section according to Embodiment 8.
Figure 27:
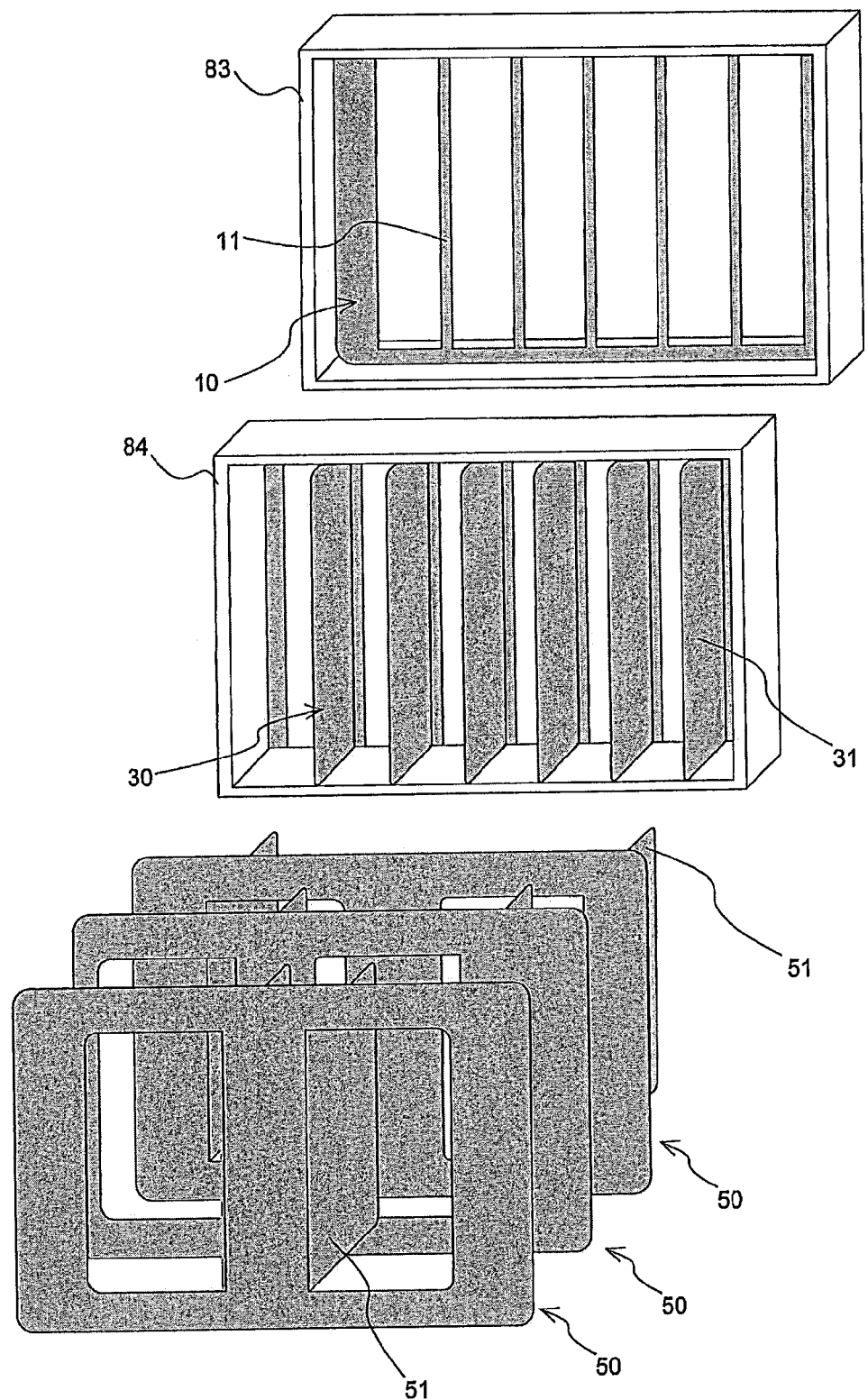
FIG. 27 is a principal perspective view illustrating the structures of the charging section and the capturing section according to Embodiment 8.

FIG. 26 is a principal schematic sectional view illustrating the structures of the charging section and the capturing section according to Embodiment 8. FIG. 27 is a principal perspective view illustrating the structures of the charging section and the capturing section according to Embodiment 8.

A charging-section high-voltage electrode unit 10 and charging-section high-voltage electrodes 11 are similar to those adopted in Embodiment 1. The charging-section high-voltage electrodes adopted in Embodiments 2 to 7 may be used. A frame-shaped insulating body 83 is provided on an outer peripheral side of the plural charging-section high-voltage electrodes 11. The insulating body 83 also functions as a wind tunnel that forms the air path 61 in an air-path housing 6.

A capturing-section high-voltage electrode unit 30 and capturing-section high-voltage electrodes 31 are similar to those adopted in Embodiment 1. The insulating body 83 is interposed between the capturing-section high-voltage electrodes 31 and the charging-section high-voltage electrodes 11 such that the capturing-section high-voltage electrodes 31 and the charging-section high-voltage electrodes 11 are not in direct contact with each other. A frame-shaped insulating body 84 is provided on an outer peripheral side of the capturing-section high-voltage electrodes 31. This insulating body 84 supports the capturing-section high-voltage electrode unit 30 and also functions as a wind tunnel that forms the air path 61 in the air-path housing 6.

A ground electrode unit 50 is formed by a combination of a plurality of ground electrodes 51. For example, the ground electrodes 51 are formed by cutting and raising a part of a single thin plate, similarly to the charging-section ground electrodes 21 illustrated in FIG. 3. In Embodiment 8, three ground electrode units 50 are superposed. This aims to ensure the length of the ground electrodes 51 in the airflow direction. That is, as described in conjunction with Embodiment 2, for example, when a plurality of ground electrodes 51 are cut out of a single flat plate, as the length of the ground electrodes 51 increases, the number of ground electrodes 51 decreases. In contrast, as the number of ground electrodes 51 increases, the length of each ground electrode 51 decreases. Since the charging section 1 and the capturing section 2 share the ground electrodes 51 in Embodiment 8, the ground electrodes 51 are required to be long enough to extend from the charging-section high-voltage electrodes 11 to the capturing-section high-voltage electrodes 31. Accordingly, the length and number of ground electrodes 51 are ensured by superposing three ground electrode units 50. This can ensure a long length of the capturing-section high-voltage electrodes 31 and can enhance the capturing effect by electric field force (coulomb force) from the charging section 1 and coulomb force from the capturing section 2. The number of ground electrode units 50 is not limited, and may be arbitrarily set in consideration of the required length and number of ground electrodes 51. The number of ground electrode units 50 is not limited to three, and may be appropriately set in consideration of, for example, the lengths in the airflow direction of the charging-section high-voltage electrodes 11 and the capturing-section high-voltage electrodes 31, the width of the air path 61, and the discharge gap length.

While the ground electrode units 50 are disposed leeward in the example of FIGS. 26 and 27, they may be disposed windward of the charging-section high-voltage electrodes 11. With this configuration, the arrangement of the ground electrode units 50 illustrated in FIGS. 26 and 27 is inverted in the airflow direction.

In this structure, when a fan 3 operates, air containing suspended particles and suspended microbes flows in the air path 61, as shown by arrows in FIG. 25. When voltage is applied from a charging high-voltage power supply 4 to the charging-section high-voltage electrodes 11, corona discharge occurs between the charging-section high-voltage electrodes 11 and the ground electrodes 51, and generates ions. The generated ions adhere to the suspended particles and suspended microbes, and the suspended particles and suspended microbes are thereby charged. When voltage is applied from a capturing high-voltage power supply 5 to the capturing-section high-voltage electrodes 31, the suspended particles and suspended microbes charged in the charging section 1 are electrically captured by the capturing section 2.

In Embodiment 8, the plural charging-section high-voltage electrodes 11 formed by thin conductive plates are arranged at intervals, and the ground electrodes 51 shaped like thin plates are disposed between the charging-section high-voltage electrodes 11 such that flat surfaces thereof are substantially parallel to the airflow in the air path 61. For this reason, the charging-section high-voltage electrodes 11 and the ground electrodes 51 are opposed to each other. This can obtain advantages similar to those of Embodiment 1, that is, it is possible to generate discharge between the charging-section high-voltage electrodes 11 and the ground electrodes 51 and to thereby charge suspended particles and suspended microbes passing through the air path 61. Further, the ground electrodes 51 disposed substantially parallel to the airflow in the air path 61 function as wind tunnels, and can induce air to the discharge portions between the charging-section high-voltage electrodes 11 and the ground electrodes 51. Hence, an advantage similar to that of Embodiment 1 can be obtained, that is, suspended particles and suspended microbes contained in the air can be charged efficiently.

Since the plural charging-section high-voltage electrodes 11 are formed by the portions remaining after a part of a conductive flat plate is cut out, the number of components is small, easy assembly is possible, and the production cost can be reduced.

Since the plural ground electrodes 51 are formed by cutting and raising a part of a flat conductive plate, the number of components is small, easy assembly is possible, and the production cost can be reduced. Further, since the ground electrodes 51 are shared by the charging section 1 and the capturing section 2, the number of components is reduced, and assembly is facilitated.

Embodiment 9

A description will be given of Embodiment 9 in which the device according to Embodiments 1 to 8 is applied to an indoor unit for an air-conditioning apparatus.

Figure 28:
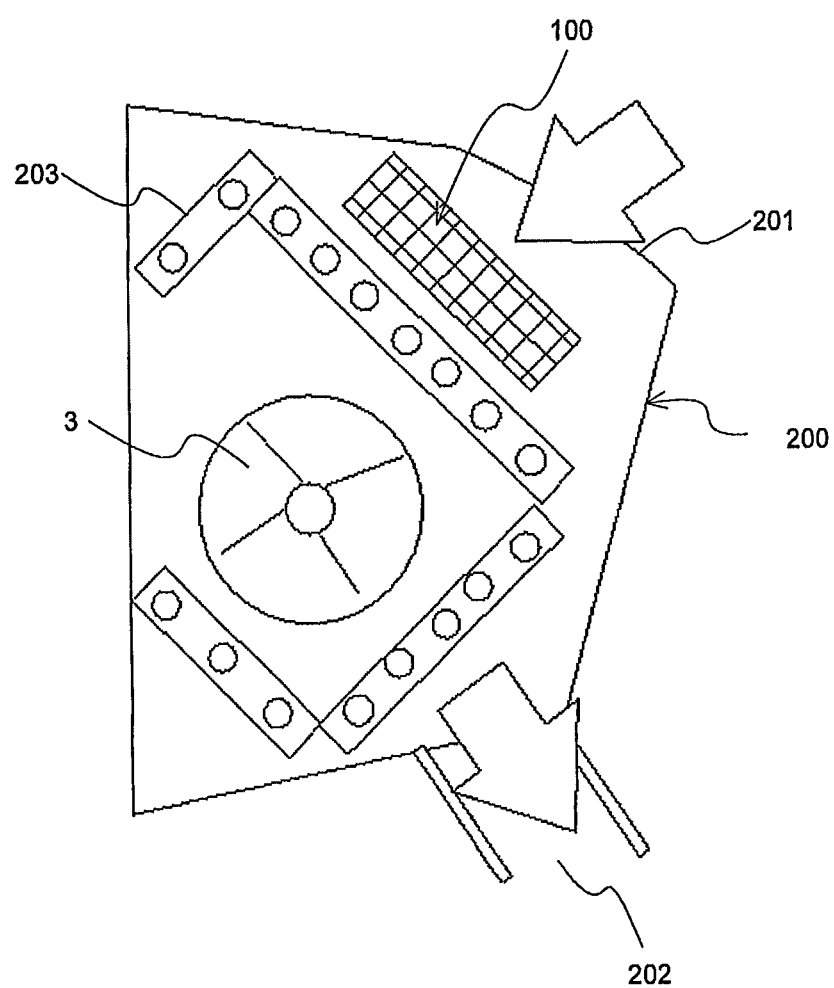
FIG. 28 is a schematic view of an indoor unit for an air-conditioning device according to Embodiment 9.

FIG. 28 is a schematic view of an indoor unit for an air-conditioning apparatus according to Embodiment 9.

As illustrated in FIG. 28, an air inlet 201 and an air outlet 202 are open in upper and lower portions of an indoor unit 200 for an air-conditioning apparatus, respectively. Within the indoor unit 200, a device 100 is provided near the air inlet 201. A fan 3 functions an air-sending device of the indoor unit 200 that blows out, from the air outlet 202, air sucked from the air inlet 201, and is formed by, for example, a cross-flow fan. Within the indoor unit 200, an air path (not illustrated) is provided to guide, to the air outlet 202, the air sucked from the air inlet 201 by the operation of the fan 3. On the air path, a heat exchanger 203 is provided.

When the fan 3 operates, air in the room is sucked from the air inlet 201, and the sucked air flows into the device 100. Suspended particles and suspended microbes contained in the air flowing in the device 100 are removed from the air, as described above in conjunction with Embodiments. Clean air from which the suspended particles and suspended microbes are removed exchanges heat in the heat exchanger 203, and is then blown out from the air outlet 202 into the room. By thus providing the device 100 in the indoor unit 200 for the air-conditioning apparatus, air to be supplied into the room can be cleaned, and the inside of the room can be kept comfortable. Further, by mounting the device 100 near the air inlet 201 serving as an inlet of air into the indoor unit 200, cleaned air is supplied to the heat exchanger 203 and so on. Hence, the inside of the indoor unit 200 can be kept clean.

While the device 100 is disposed upstream of the heat exchanger 203 near the air inlet 201 in Embodiment 9, it may be disposed near a position upstream of the air outlet 202 of the indoor unit 200. With this configuration, air, from which contained suspended particles and suspended microbes are removed, can also be supplied into the room.

Instead of the device 100, only the charging section 1 adopted in Embodiments 1 to 8 may be provided in the indoor unit 200. Suspended particles and suspended microbes can be captured by the charging-section ground electrodes 21 of the charging section 1, as described above in conjunction with Embodiment 1. Hence, when only the charging section 1 is provided, the removal rate of suspended particles and suspended microbes is slightly lower than when the capturing section 2 is provided, but the inside of the indoor unit 200 and the inside of the room can be kept comfortable.

While the device 100 is provided in the indoor unit 200 for the air-conditioning apparatus in Embodiment 9, it may be provided in an air purifier, a television, a vacuum cleaner, and a ventilator. By directly mounting the device 100 in an air-conditioning air duct, suspended particles and suspended microbes can be removed from air to be taken into the room.

While suspended particles and suspended microbes charged by the charging section 1 are captured by the electrodes of the capturing section 2 in Embodiments described above, a filter for capturing suspended particles and suspended microbes may be provided downstream of the charging section 1 instead of the electrodes of the capturing section 2.

REFERENCE SIGNS LIST

1: charging section, 2: capturing section, 3: fan, 4: charging high-voltage power supply, 5: capturing high-voltage power supply, 6: air-path housing, 7: insulator, 8: insulating body, 9: spacer, 10: charging-section high-voltage electrode unit, 10A: charging-section high-voltage electrode unit, 10Aa: charging-section high-voltage electrode unit, 10Ab: charging-section high-voltage electrode unit, 10B: charging-section high-voltage electrode unit, 11: charging-section high-voltage electrode, 11B: charging-section high-voltage electrode, 11a: short side, 11b: connecting portion, 11c: connecting portion, 12: support portion, 13: frame portion, 14: folded piece, 15: power feed plate, 20: charging-section ground electrode unit, 20a: charging-section ground electrode unit, 20b: charging-section ground electrode unit, 21: charging-section ground electrode, 22a: cutting line, 22b: bending line, 23: frame portion, 30: capturing-section high-voltage electrode unit, 31: capturing-section high-voltage electrode, 41: capturing-section ground electrode, 50: ground electrode unit, 51: ground electrode, 61: air path, 62: frame member, 81: aperture, 82: groove, 83: insulating body, 84: insulating body, 100: device, 200: indoor unit, 201: air inlet, 202: air outlet, 203: heat exchanger.

The invention claimed is:

1. A corona discharge device comprising:

an air-path housing having an air path therein;

a discharge electrode unit including a plurality of first discharge electrodes each of which is formed by either of thin wire and flat plate having conductivity; and two counter electrode units formed by a conductive flat plate, wherein each of the counter electrode units includes a plurality of uniformly shaped counter electrodes formed by flat plates, the plurality of counter electrodes of one of the counter electrode units are disposed between the counter electrodes of the other counter electrode unit, the plurality of first discharge electrodes are arranged at intervals in a direction intersecting an airflow in the air path, and are connected to one another at at least one longitudinal end by a conductive frame, the plurality of counter electrodes of the two counter electrode units are disposed between the first discharge electrodes in an orientation such that flat surfaces thereof are substantially parallel to the airflow in the air path, the plurality of counter electrodes are connected to one another at at least one longitudinal end by a conductive frame, and the counter electrodes and the first discharge electrodes are alternately arranged in the direction intersecting the airflow in the air path so as to be spaced apart from each other.

2. The corona discharge device of claim 1, wherein a length of portions of the counter electrodes downstream of the first discharge electrodes in a direction of the airflow is more than or equal to double a discharge gap length between the counter electrodes and the opposed first discharge electrodes.

3. The corona discharge device of claim 1, wherein a pair of the counter electrodes provided at both ends, of the plurality of counter electrodes, form a part of a side wall of the air path.

4. The corona discharge device of claim 1, wherein the plurality of first discharge electrodes are formed by a portion remaining after a part of a conductive plate member having a thickness of 0.05 mm to 0.5 mm is cut out.

5. The corona discharge device of claim 1, wherein the plurality of counter electrode are formed by cutting and raising a part of a plate member made of a conductive material.

6. The corona discharge device of claim 1, wherein the frame of the discharge electrode unit and the frame of the counter electrode units are superposed in a direction of the airflow with an insulating material being disposed therebetween, and the frame of the discharge electrode unit is covered with thermosetting resin.

7. An air-conditioning apparatus comprising:

a corona discharge device including:

an air-path housing having an air path therein, a discharge electrode unit including a plurality of first discharge electrodes each of which is formed by either of thin wire and flat plate having conductivity, and two counter electrode units formed by a conductive flat plate, wherein each of the counter electrode units includes a plurality of uniformly shaped counter electrodes formed by flat plates, the plurality of counter electrodes of one of the counter electrode units are disposed between the counter electrodes of the other counter electrode unit, the plurality of first discharge electrodes are arranged at intervals in a direction intersecting an airflow in the air path, and are connected to one another at at least one longitudinal end by a conductive frame, the plurality of counter electrodes of the two counter electrode units are disposed between the first discharge electrodes in an orientation such that flat surfaces thereof are substantially parallel to the airflow in the air path, the plurality of counter electrodes are connected to one another at at least one longitudinal end by a conductive frame, and the counter electrodes and the first discharge electrodes are alternately arranged in the direction intersecting the airflow in the air path so as to be spaced apart from each other.

* * * * *